United States Patent
Singh et al.

(10) Patent No.: US 8,961,188 B1
(45) Date of Patent: Feb. 24, 2015

(54) SYSTEM AND METHOD FOR CLINICAL PATIENT CARE SIMULATION AND EVALUATION

(75) Inventors: Anurag Singh, Exton, PA (US); Sarita Joshi, Malvern, PA (US); Senthamarai Kannan Ayyakkannu, West Chester, PA (US); David Leon Houseman, Chester Springs, PA (US)

(73) Assignee: Education Management Solutions, Inc., Exton, PA (US)

( * ) Notice: Subject to any disclaimer, the term of this patent is extended or adjusted under 35 U.S.C. 154(b) by 714 days.

(21) Appl. No.: 13/153,191

(22) Filed: Jun. 3, 2011

(51) Int. Cl.
G09B 23/28 (2006.01)

(52) U.S. Cl.
USPC .......................................................... 434/262

(58) Field of Classification Search
CPC ....................................................... G09B 23/28
USPC ................................................................ 434/262
See application file for complete search history.

(56) References Cited

U.S. PATENT DOCUMENTS

| | | | |
|---|---|---|---|
| 5,867,821 A | 2/1999 | Ballantyne et al. | |
| 6,077,082 A | 6/2000 | Gibson et al. | |
| 6,226,620 B1 | 5/2001 | Oon | |
| 6,272,468 B1 | 8/2001 | Melrose | |
| 6,298,326 B1 | 10/2001 | Feller | |
| 6,443,735 B1 | 9/2002 | Eggert et al. | |
| 6,918,771 B2 | 7/2005 | Arington et al. | |
| 7,277,874 B2 | 10/2007 | Sumner, II et al. | |
| 7,593,967 B2 | 9/2009 | Harnsberger et al. | |
| 7,693,697 B2 | 4/2010 | Westenskow et al. | |
| 7,725,328 B1 | 5/2010 | Sumner, II et al. | |
| 7,777,763 B2 | 8/2010 | Haakonsen et al. | |
| 7,801,740 B1 | 9/2010 | Lesser | |
| 7,840,512 B2 | 11/2010 | Pandya et al. | |
| 7,877,277 B1 | 1/2011 | Petit et al. | |
| 7,885,822 B2 | 2/2011 | Akers et al. | |
| 2004/0009459 A1* | 1/2004 | Anderson et al. ............. | 434/262 |
| 2004/0161731 A1* | 8/2004 | Arington et al. .............. | 434/262 |
| 2004/0243545 A1* | 12/2004 | Boone et al. ....................... | 707/2 |
| 2005/0131663 A1* | 6/2005 | Bangs et al. ..................... | 703/11 |
| 2006/0084043 A1 | 4/2006 | Weaver et al. | |

(Continued)

OTHER PUBLICATIONS

Stanford School of Medicine's Standardized Patient Program (http://med.stanford.edu/ome/spp/).*

(Continued)

Primary Examiner — Robert J Utama
Assistant Examiner — Elroy S Crocker
(74) Attorney, Agent, or Firm — Rosenberg, Klein & Lee

(57) ABSTRACT

An evaluation system and method are provided for simulating clinical care of a virtual patient. A database of electronic medical records (EMRs) is established, with at least one EMR including a plurality of EMR items collectively profiling the virtual patient. A simulation management unit coupled to the database includes a plurality of selectively executable control modules. At least one control module defines a simulation scenario; and, at least one other control module generates a duplicate EMR of the virtual patient for each of a plurality of simulation participants. At least one evaluator station establishes interactive interface for an evaluator. A plurality of participant stations establish interactive access for the simulation participants to a corresponding one of the duplicate EMRs during a simulated clinical encounter with the virtual patient. The simulation management unit independently updates the duplicate EMRs for the simulation participants responsive to clinical actions respectively taken by those participants.

29 Claims, 27 Drawing Sheets

(56) References Cited

U.S. PATENT DOCUMENTS

| | | |
|---|---|---|
| 2008/0014566 A1 | 1/2008 | Chapman et al. |
| 2009/0089100 A1 | 4/2009 | Nenov et al. |
| 2009/0150134 A1* | 6/2009 | De Leon et al. ............... 703/11 |
| 2010/0092936 A1 | 4/2010 | Pfingsten et al. |
| 2010/0131434 A1 | 5/2010 | Magent et al. |
| 2010/0235378 A1 | 9/2010 | Armstrong et al. |
| 2010/0266998 A1* | 10/2010 | Tashiro et al. ............... 434/262 |

OTHER PUBLICATIONS

Stanford School of Medicines's Standardized Pateint Program (http://med.stanford.edu/ome/spp/).*

* cited by examiner

Manage EMR Patients
*Update patient information below. Click on the save button when you are done.*

Name:* Aretha Franklin
Gender: Female ▼
Date of Birth: 11/20/1949 (mm/dd/yyyy)
Age: 61 Years [Calculate]
Status: Active ▼

*Search Documents from the library and press the plus icon to map the document to the patient.*

Keywords: [ ] [Search]

[Cancel] [Save]

91 — (patient info section)
92 — EMR Documents Available

| Document Name | Add |
|---|---|
| Add Lab Reports | ✚ |
| Adult Assessment – Neurological | ✚ |
| Adult Assessment – Psychosocial & Education | ✚ |
| Adult Assessment – Respiratory | ✚ |
| Adult Assessment – GI & GU | ✚ |
| EMS Allergy Log | ✚ |
| EMS Daily Food Diary | ✚ |

93 — Search

94 — EMR Documents added

| Document Name | Delete |
|---|---|
| Adult Assessment – Cardiovascular & Neurovascular | 🗑 |
| Adult Assessment – Neurological | 🗑 |
| Adult Assessment – Musculoskeletal & Integumentary | 🗑 |
| Adult Assessment – Safety & Skin Care Activity | 🗑 |
| EMS 24 hour Nursing Flow | 🗑 |

FIG. 9

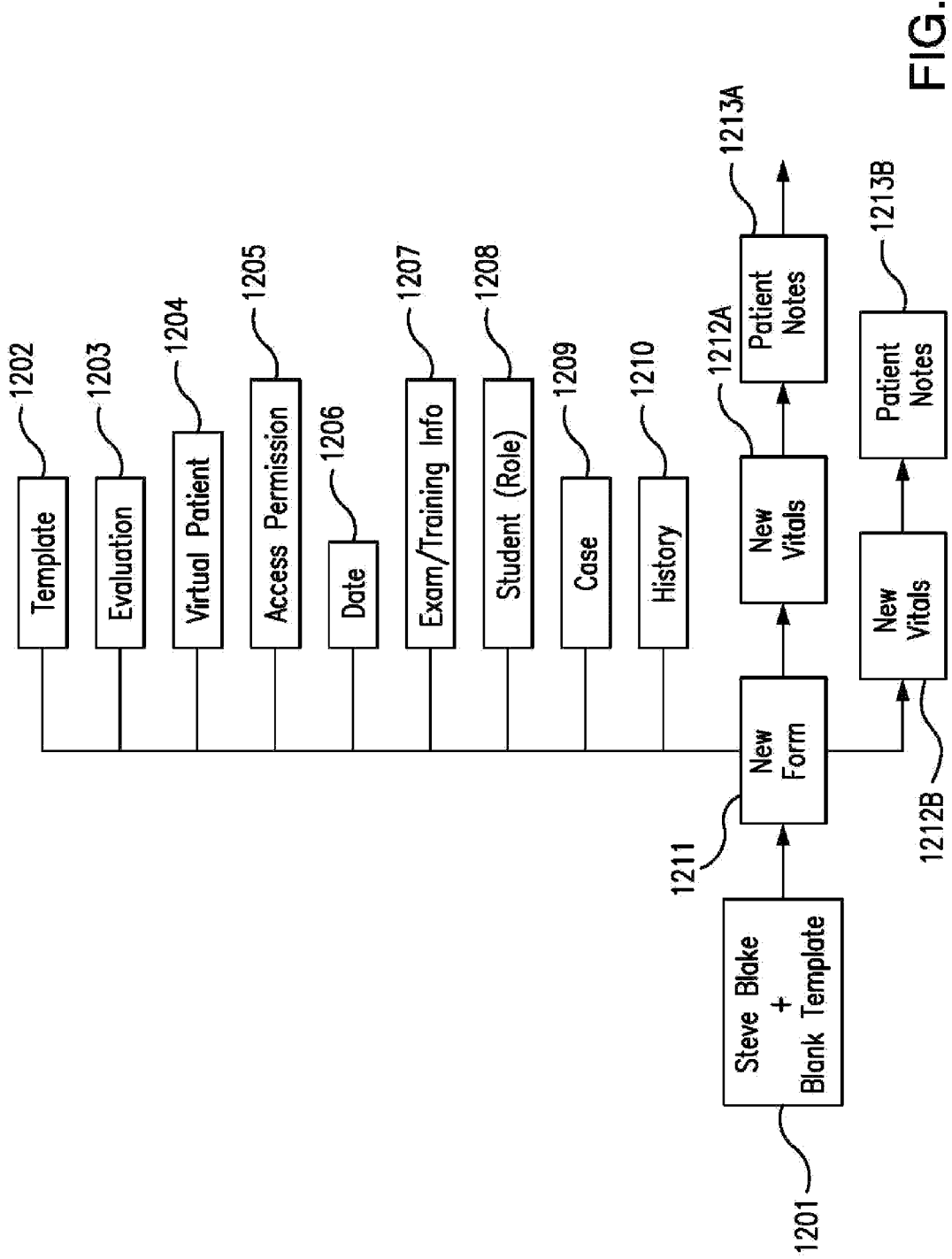

Welcome to EMS Institute

Logout | Home | ⓘ Help

ARCADIA

Admin  Users  Case  SP  Student  Session  Score Reports  Video  Simulation  Inventory

1801

Cases  18011
○ Cases   ○ Item Library   ○ Item Category   ○ Multiple Choice   ○ Multimedia   ○ Competency Skill Groups
○ Category Groups   ○ Land Reports   ○ SP Case Assistant   ○ EMR Patient  18020

Dashboard   My Favorites

Iministrator

⊗  Welcome to EMS Institute

Click here to edit the welcome message displayed in the login page.

○ Todays Sessions

11:00 AM : RecnggSes19
11:45 AM : future
...More

Latest Updates

Edit Latest Updates

○ Upcoming Sessions

6/8/2011 09:00 AM – Test To Copy
...More

Upcoming Events

Edit Events

○ Last Viewed

Case:    20th november    Session:   05/19/2011 9:00 AM–Suruchi 808
Scenario: A Vivek Scenrio   Schedule: 05/16/2011 1:00 AM–kal 1

Survey

EMS Copyright 2010 Education Management Solutions. All rights reserved. Application Version: 4.86.5.111 (Release No: 680)

FIG. 18

Wecome to EMS Institute

Logout | Home | ⓘ Help

ARCADIA

Admin  Users  Case  SP  Student  Session  Score  Reports  Video  Simulation  Inventory

1901

Pending 19011  ○ Item Library  ○ Payment  ○ Profile  ○ Training  ○ Search

Iministrator

○ Log  ○ Profile Questions  19018

Welcome to EMS Institute

Dashboard  My Favorites

Click here to edit the welcome message displayed in the login page.

○ Todays Sessions

11:00 AM : RecnggSes19
11:45 AM : future
...More

Latest Updates

Edit Latest Updates

○ Upcoming Sessions

6/8/2011 09:00 AM – Test To Copy
...More

Upcoming Events

Edit Events

○ Last Viewed

Case: 20th november    Session: 05/19/2011 9:00 AM-Suruchi 808
Scenario: A Vivek Scenrio   Schedule: 05/16/2011 1:00 AM-kal 1

Survey ems Copyright 2010 Education Management Solutions. All rights reserved. Application Version: 4.86.5.111 (Release No: 680)

```
                                              Logout | Home | ⓘ Help
2401    Wecome to EMS Institute
                                                        ARCADIA

[icons]   Admin Users Case SP Student Session Score Reports Video Simulation Inventory
           ○ Playback  ○ Live Video  ○ Camera Control  ○ Video Access  ○ Bookmark Groups  ○ Bookmark Images Iministrator
 ○ BackupETCVideos    24017
      24011
                                                        Welcome to EMS Institute
      Dashboard   My Favorites
                                                        Click here to edit the welcome
 ○ Todays Sessions                                      message displayed in the login
                                                        page.
  11:00 AM : RecnggSes19
  11:45 AM : future              ...More                Latest Updates Edit Latest Updates
 ○ Upcoming Sessions
                                                        Upcoming Events
  6/8/2011 09:00 AM – Test To Copy   ...More
                                                        Edit Events
 ○ Last Viewed
                                                        Survey
  Case:      20th november   Session:  05/19/2011 9:00 AM-Suruchi 808
  Scenario:  A Vivek Scenrio  Schedule: 05/16/2011 1:00 AM-kal 1

EMS  Copyright 2010 Education Management Solutions. All rights reserved. Application Version: 4.86.5.111 (Release No: 680)
```

FIG. 24

Wecome to EMS Institute 2501

Admin  Users  Case  SP  Student  Session  Score  Reports  Video  Simulation  Inventory
○ MonthViewCalendar   ○ Schedule Request   ○ Schedule Scenario   ○ All Scenarios   ○ Email Events
25011                                                                          25015

Welcome to EMS Institute
Dashboard    My Favorites

○ Todays Sessions
11:00 AM : RecnggSes19
11:45 AM : future                                              ...More ○ Upcoming Sessions
6/8/2011 09:00 AM – Test To Copy                               ...More ○ Last Viewed
Case:     20th november        Session:   05/19/2011 9:00 AM–Suruchi 808
Scenario: A Vivek Scenrio      Schedule:  05/16/2011 1:00 AM–kal 1

Logout | Home | ⊙ Help

ARCADIA

Welcome administrator

Welcome to EMS Institute

Click here to edit the welcome message displayed in the login page.

Latest Updates

Edit Latest Updates

Upcoming Events

Edit Events

Survey

EMS  Copyright 2010 Education Management Solutions. All rights reserved. Application Version: 4.86.5.111 (Release No: 680)

FIG. 25

Wecome to EMS Institute 2601

Admin  Users  Case  SP  Student  Session  Score  Reports  Video  Simulation  Inventory
○ Equipment   ○ Rooms           ○ Room Settings      ○ Export/Import
   26011                                                  26014

Logout | Home | ⓘ Help

ARCADIA

Welcome administrator

Welcome to EMS Institute

Dashboard   My Favorites

Click here to edit the welcome message displayed in the login page.

○ Todays Sessions

11:00 AM : RecnggSes19
11:45 AM : future                              ...More

Latest Updates

Edit Latest Updates

○ Upcoming Sessions

6/8/2011 09:00 AM — Test To Copy               ...More

Upcoming Events

Edit Events

○ Last Viewed

Case:     20th november    Session:  05/19/2011 9:00 AM-Suruchi 808
Scenario: A Vivek Scenrio  Schedule: 05/16/2011 1:00 AM-kal 1

Survey

EMS Copyright 2010 Education Management Solutions. All rights reserved. Application Version: 4.86.5.111 (Release No: 680)

FIG. 26

SYSTEM AND METHOD FOR CLINICAL PATIENT CARE SIMULATION AND EVALUATION

BACKGROUND OF THE INVENTION

1. Field of the Invention

The present invention is generally directed to a system and method for simulating and evaluating the clinical care of a patient. More specifically, the present invention is directed to a system and method for establishing a simulated environment based on electronic medical records for interactive clinical instruction in patient care. The system and method provide for the use of virtual patients profiled by electronic medical records (EMR) in simulating their clinical treatment by a plurality of simulation participants, and for the comparative evaluation of the diagnostic, therapeutic, or other treatment actions taken by a group of simulation participants on the same virtual patient. The comparative evaluation for the participants may be relative to one another as well as to an idealized course of treatment administered to a virtual patient. The system and method afford each participant the opportunity to independently undertake treatment actions upon his/her own cloned version of the virtual patient having a certain base, or starting condition indicated by its EMR. The system and method maintain and independently track the conditions of the cloned virtual patients and corresponding EMR's as they are subjected to their assigned participants' clinical treatment actions. Additions, entries, and updates made by simulation participants to the EMR of their virtual patient clones may then be examined for objective evaluation by an instructor or other overseer.

2. Description of the Related Art

In the field of interactive education, and particularly in the field of simulators and interactive clinical education, it is important to allow participants, such as physicians, surgeons, nurses, medical technicians, assistants, students, and the like, to not only learn their intended profession passively by reading and listening to books, publications, and instructors, but also to perform diagnostic and therapeutic tasks and procedures that will be critical to their eventual practice upon completion of their education. However, there is clearly a great risk that allowing students to practice on actual patients may lead to complications, accidents, mistakes, and even potentially deaths. Obviously, allowing a mere student to practice medicine on an actual living patient would be a very high risk activity—if not outright reckless. A mere student is not in possession of the experience or wisdom of a practiced professional. Thus, a catch-22 exists, whereby a student is initially unqualified and lacks the experience necessary to perform actual tasks which are needed to gain that very experience and qualification.

Thus, there is a need for a method and system for establishing a simulated environment whereby clinical patient care experiences may be gained and suitably evaluated. There is a need for interactively evaluating and instructing participants in this regard, by use of electronic medical records kept for virtual patients in an environment emulating actual clinical conditions.

SUMMARY OF THE INVENTION

An object of the present invention is to provide a system and method for interactive education for independently tracking and grading participant's interactions with electronic medical records (EMRs) and virtual patients.

It is another object of the present invention to provide a system and method for progressively simulating clinical care of a persistent virtual patient.

Yet another object of the present invention is to provide a system and method of interactively simulating and evaluating clinical care of a virtual patient.

These and other objects are attained by a system and method implemented in accordance with the present invention. An evaluation system is provided in certain embodiments for simulating clinical care of a virtual patient. The system generally comprises a database of electronic medical records, with at least one of the electronic medical records (EMR) including a plurality of EMR items collectively profiling the virtual patient. A simulation management unit is coupled to the database which includes a plurality of selectively executable control modules. At least a first of the control modules is executable to define a simulation scenario with respect to the virtual patient; and, at least a second of the control modules is executable to generate a duplicate EMR of the virtual patient for each of a plurality of simulation participants. At least one evaluator station is operably coupled to the simulation management unit which serves to establish interactive interface for an evaluator. A plurality of participant stations are also operably coupled to the simulation management unit. Each participant station establishes interactive access for one of the simulation participants to a corresponding one of the duplicate EMRs during a simulated clinical encounter with the virtual patient. The simulation management unit independently updates the duplicate EMRs for the simulation participants responsive to clinical actions respectively taken by those simulation participants based on the simulated clinical encounters with the virtual patient.

From another aspect, a system for interactive educational simulation of clinical care for a virtual patient includes a database of electronic medical records. At least one electronic medical record (EMR) includes a plurality of EMR items collectively profiling the virtual patient in a base condition. A simulation management unit is operatively coupled to the database. The simulation management unit includes a plurality of selectively executable control modules. At least a first control module is executable to define a simulation scenario with respect to the virtual patient. At least a second control module is executable to generate, for a plurality of students, a respective plurality of duplicate EMRs each corresponding to a clone of the virtual patient in the base condition. At least one faculty station is operably coupled to the simulation management unit. The faculty station establishes interactive interface thereto for an instructor. A plurality of student stations are operably coupled to the simulation management unit, each student station establishes interactive access for one of the students to a corresponding one of the duplicate EMRs during a simulated clinical encounter with one of the virtual patient clones. The simulation management unit independently updates duplicate EMRs for each virtual patient clone according to a clinical action responsively taken by a corresponding student based on the simulated clinical encounter therewith— an independently updated EMR being thereby generated for each of the virtual patient clones.

From another aspect, a system for interactive progressive simulation of clinical care for a persistent virtual patient includes a database of electronic medical records. At least one electronic medical record (EMR) includes a plurality of EMR items collectively profiling the virtual patient in a base condition. A simulation management unit is coupled to the database with the simulation management unit including a plurality of selectively executable control modules. At least a first of the control modules are executable to define a simulation scenario with respect to the virtual patient. At least a second of the control modules is executable to respectively generate, for a plurality of simulation participants, a plurality of duplicate EMRs corresponding to clones of the virtual patient in the base condition. At least one evaluator station is operably coupled to the simulation management unit. The evaluator station establishes interactive interface to the simulation management unit for an evaluator. A plurality of simulation participant stations are operably coupled to the simulation management unit as well. Each of the simulation participant stations establishes interactive access for one of the simulation participants to a corresponding one of the duplicate EMRs during a simulated clinical encounter with one of the virtual patient clones. The simulation management unit independently updates the duplicate EMR for each of the virtual patient clones according to a clinical action responsively taken by a corresponding simulation participant based on the simulated clinical encounter therewith, an independently updated EMR being thereby generated for each of the virtual patient clones. The simulation management unit maintains the updated EMR of at least one selected virtual patient clone in the database to define the base condition of the virtual patient for a subsequent simulation scenario. The second control module thereby generates the plurality of duplicate EMRs to correspond in the subsequent simulation scenario to further clones of the selected virtual patient.

From yet another aspect, a method of interactively simulating and evaluating clinical care of a virtual patient includes establishing a database of electronic medical records. At least one electronic medical record (EMR) includes a plurality of EMR items collectively profiling the virtual patient. A simulation management unit established in a processor operably coupled to the database is actuated; the simulation management unit actuation includes selective execution of a plurality of control modules programmed therein. At least a first of the control modules is selectively executed to define a simulation scenario with respect to the virtual patient. At least a second of the control modules is selectively executed to generate a duplicate EMR of the virtual patient for each of a plurality of simulation participants. At least one interactive evaluator station interface to the simulation management unit is maintained. For each of the simulation participants, an interactive participant station interface to the simulation management unit is established, each of the simulation participants thereby having interactive access to a corresponding one of the duplicate EMRs during a simulated clinical encounter with the virtual patient. The simulation management unit independently updates the duplicate EMRs for the simulation participants responsive to clinical actions respectively taken thereby based on the simulated clinical encounters with the virtual patient.

From yet another aspect, a method for progressively simulating clinical care of a persistent virtual patient includes establishing a database of electronic medical records with at least one electronic medical record (EMR) including a plurality of EMR items collectively profiling the virtual patient in a base condition. A simulation management unit established in a processor operably coupled to the database is actuated; the simulation management unit actuation including selective execution of a plurality of control modules programmed therein. At least a first of the control modules is executable to define a simulation scenario with respect to the virtual patient. At least a second of the control modules is executable to respectively generate, for a plurality of simulation participants, a plurality of duplicate EMRs corresponding to clones of the virtual patient in the base condition. At least one evaluator station interface to the simulation management unit is maintained. Each of the simulation participants has an interactive participant station interface to the simulation management unit established. Each of the simulation participants is thereby granted interactive access to a corresponding one of the duplicate EMRs during a simulated clinical encounter with a virtual patient clone. The duplicate EMR for each of the virtual patient clones is independently updated according to a clinical action responsively taken by a corresponding simulation participant based on the simulated clinical encounter therewith. An independently updated EMR is thereby generated for each of the virtual patient clones. The updated EMR of at least one of the virtual patient clones selected for persistent simulation are selectively maintained. The updated EMR of the selected virtual patient clone defines the virtual patient base condition for a subsequent simulation scenario. The second control module thereby generates the plurality of duplicate EMRs to correspond in the subsequent simulation scenario to further clones of the selected virtual patient.

BRIEF DESCRIPTION OF THE DRAWINGS

FIG. 9 is an exemplary screen shot of a system in accordance with an embodiment of the present invention;

FIG. 12 is a simplified flow diagram of a method of interactive simulation and evaluation in accordance with an embodiment of the present invention;

FIGS. 15-26 are exemplary screen shots of a system in accordance with an embodiment of the present invention.

DETAILED DESCRIPTION OF THE PREFERRED EMBODIMENTS

Figure 1:
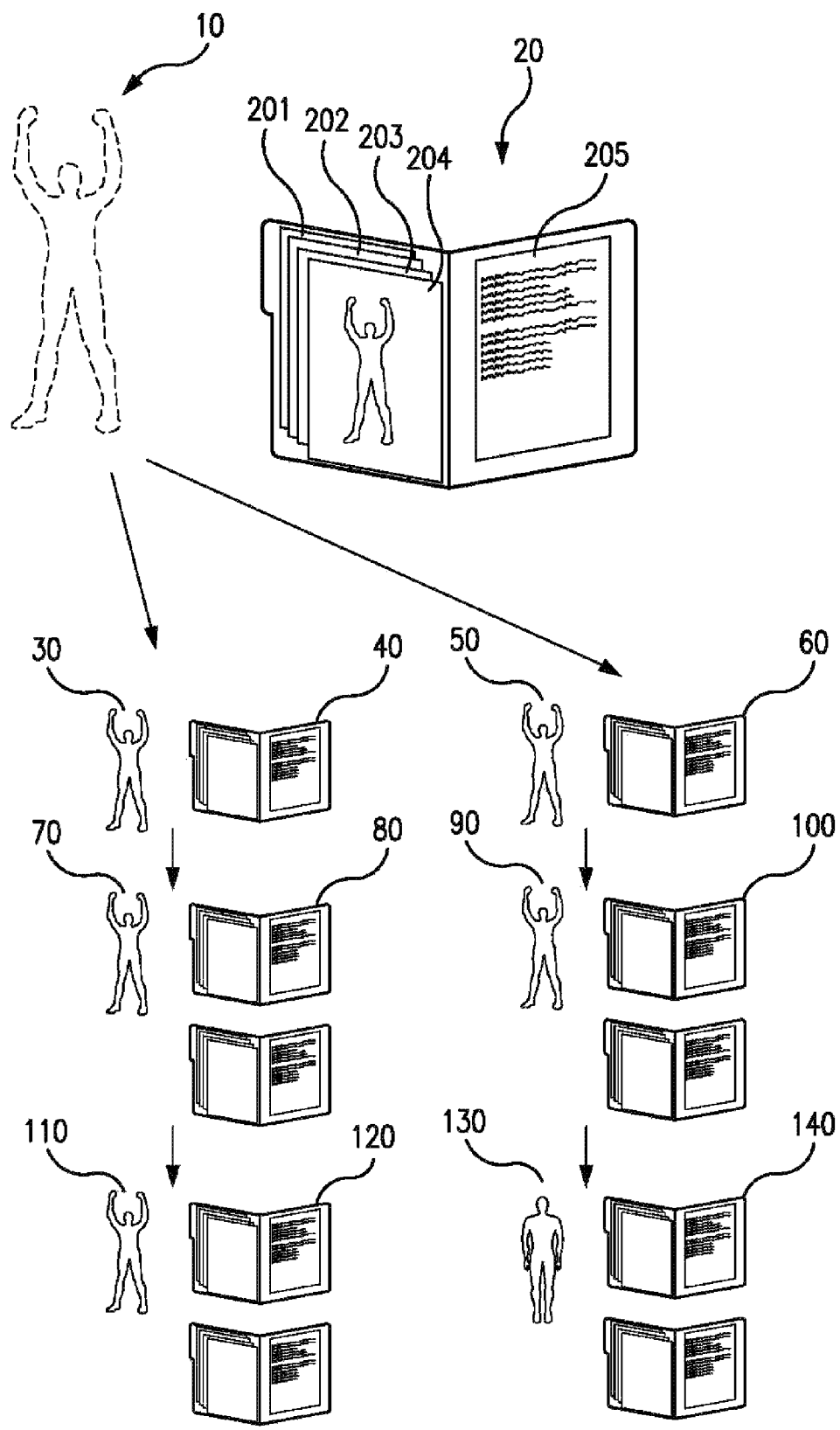
FIG. 1 is a flow diagram of a method of interactive simulation and evaluation of clinical care for a plurality of cloned virtual patients in accordance with one exemplary embodiment of the present invention.

In the field of simulators, interactive education, and particularly with respect to medical education simulators, it is essential to provide students or trainees with experiential tools which closely simulate real world conditions, interactions with patients, manipulations of electronic medical records (EMR), various other actual real-world interactions, and thereafter provide them with meaningful evaluative feedback.

In accordance with an embodiment of the present invention, a system and method for interactive simulation and evaluation of clinical care for a plurality of cloned virtual patients is provided. In broad concept, an instructor, faculty member, administrator, or other such evaluator (used interchangeably herein) selects EMR items from a bank of forms and media such as X-ray images, CAT scan images, lab results, and the like, to establish an EMR-based profile for one or more virtual patients.

The instructor may, in advance, select an appropriate diagnosis or scenario which the participants are to evaluate and aspire towards diagnosing and/or treating correctly. Additionally, the instructor may define a set of ideal states for the EMR as a participant progresses through a certain scenario. Once a virtual patient, EMR, and target diagnosis have been established, an evaluator may then effectively clone the virtual patient by duplicating multiple versions of the EMR. Each of the duplicated or cloned virtual patients may then be assigned to the simulated clinical care of a selected participant. In certain alternative embodiments, a common virtual patient may be assigned to the simulated clinical care of a group of participants in a collaborative simulation scenario.

The instructor, or other such evaluator overseeing the exercise, may then specify at least a portion of the EMR to be made available to the participant in advance of an actual encounter, and then such portion of the EMR is indeed provided to each participant for their review. Preferably, the simulation experience is supplemented by an actual clinical encounter with a real-life version of the virtual patient (either a role-playing actor or a manikin). The encounter would simulate an actual clinical examination, where the participant engages in live interface with the virtual patient's stand-in. For his/its part, the stand-in purports to exhibit certain predetermined symptoms of interest, provides scenario-appropriate feedback to the attending participant, and may even provide relevant explanations and 'personal' history information to the participant when prompted. The attending participant is naturally afforded an opportunity during the process to take necessary notes, ask pertinent questions and/or make responsive entries/additions/updates to the EMR, by for instance entering notes, prescribing therapeutic actions, and/or ordering tests such as X-rays, CAT scans, blood tests, and the like. Each of the participant's responsive entries/updates to the EMR and other responsive actions are preferably captured and recorded, so as to be maintained and tracked independent of other participants.

Modifiable forms may be presented to the participant to enable them to gain actual experience in EMR, and each modified form may be stored as part of the simulation record—to be later evaluated. In one exemplary embodiment, one or more known configurations such as that of Microsoft INFOPATH® forms are used to maintain templates and generate customized forms for each participant encounter. However, modifiable forms may be generated and maintained in any suitable manner known in the art—for example, by use of fillable .PDF files, extensible markup language (XML) files, and the like.

At this stage, the evaluator or instructor may suitably evaluate and even grade the participant's actions, and/or responsive additions to the EMR. For example, the evaluator may compare them to a model ideal addition/update or to certain predetermined idealized states for the EMR, or, even by comparing a particular participant's responses relative to a composite of the other participant's responsive additions and/or responses. Objective checklists may also be factored into an evaluation—as may surveys and other indicia of performance. Where the resources of a particular application permit, some or all of the evaluation and grading process may be automated. The required evaluation/grading criteria would be programmably implemented and applied in suitable manner to the information respectively captured for the simulation participants.

In accordance with certain aspects of the present invention, a virtual patient is effectively cloned by duplicating his/her corresponding EMR, and each cloned version of that virtual patient is assigned to one participant. Any physiological responses to therapeutic actions taken by a particular participant are then manifest in his/her cloned version of the virtual patient. These responses are reflected in further updates to the EMR which are recorded and preferably tracked. For example, if the participant prescribed a certain course of action, such as a regimented dieting program, the EMR of the respective virtual patient clone may be updated to reflect weight loss, reduced blood pressure, or other factors reflecting probable results of the prescribed course of action by the participant. One or more such virtual patient clones may be persistently maintained—not being deleted upon completion of one simulation scenario or encounter, but rather, may span a series of scenarios and may even follow a student throughout the student's matriculation. A persistent virtual patient, having an accumulated history of such virtual 'treatment,' would also be available as a subject for further simulation scenarios to other students as well.

Also provided in the interactive simulation is an integrated scheduling component. Preferably, this component is operable to perform logistical coordination of manikins (anatomic mannequins for medical education), actors, simulation rooms, necessary medical equipment, infrastructure related to capture of the participant's performance, as well as participant schedules and requirements.

Turning now to FIG. 1, there is shown a simplified flow diagram illustrating an exemplary method of interactive simulation and evaluation of clinical care for a plurality of cloned virtual patients. A virtual patient 10 is created or copied from another virtual patient or even modeled after a real patient (though suitably anonymized to be in accord with HIPAA regulations and privacy expectations of patients). Real-world case studies of actual patients presenting symptoms and successful or unsuccessful treatment paths may indeed be harnessed for simulations in this manner.

An electronic medical record (EMR) 20 is also generated or copied and suitably anonymized to correspond with the virtual patient 10. The EMR 20 may contain a plurality of EMR items 201, 202, 203, 204, and 205, each representing potentially a previous history of treatment, including encounters with a healthcare provider, documented by practitioner notes, test results, and/or other information related to the virtual patient 10. The virtual patient 10 may be effectively cloned to yield a plurality of virtual patient clones 30 and 50, substantially identical to one another and having respective, independently maintainable EMRs 40 and 60.

At this point, preferably, each virtual patient clones 30, 50 and electronic medical records (EMR) 40, 60 are substantially identical. Each participant is provided with their own unique virtual patient 30/50 and EMR 40/60 pair. The participants may be allowed to review the EMR for their virtual patient 30, 40 in advance of an encounter which will be subsequently scheduled. During an encounter with the virtual patient 30, a participant reviews an EMR, may ask questions of the virtual patient, may note observations, order tests, and the like.

In an optional embodiment, the virtual patients 70 and 90 and their respective EMR 80 and 100 may change in response to external stimuli or the participant's recommendations, prescriptions, and/or responsive actions. Such evolving conditions of the virtual patients 70 and 90 may be extrapolated based on the intended scenario by the instructor or evaluator. Additionally, the EMRs 80 and 100 may be updated and/or have additional information added, such as if the participant had referred the virtual patient 70 or 90 to a specialist, nurse, therapist, or other caregiver for additional tests or treatment. The virtual patient 70, for example, would only respond to stimuli applied to that same virtual patient 30 (which is virtual patient 70 but pre-encounter). Similarly, virtual patient 90 would only change responsive to additions or modifications to that very same virtual patient 50 (pre encounter).

Virtual patient 70 would not respond to stimuli applied to virtual patient 50; similarly, virtual patient 90 would not respond to stimuli applied to virtual patient 30. Each individual participant or student is assigned a corresponding virtual patient and EMR and the student's actions and/or additions are maintained and tracked independently of each other participant or student.

Each participant or student may indeed have one or a series of subsequent encounters with a respective virtual patient 70, 90. Such virtual patients 70, 90 may indeed maintain a changing history, EMR, and condition responsive to passing of time, external stimuli, and/or a participant's therapeutic actions enacted on that virtual patient. In a subsequent encounter with the virtual patient 70 or 90, the virtual patient's 70 or 90 condition may have changed and may be reflected in the patient's current condition. Following a secondary or subsequent encounter, virtual patient 110 may for example have recovered completely while virtual patient 130 assigned to a different participant may indeed have a completely different condition, where the original condition may have worsened or the patient may have died. Unlike real-world conditions, the death of a virtual patient is of no concern—aside, potentially, from detriment to the student's grade; whereas a real-world encounter between student and patient may have very grave and serious ramifications for all involved.

For an example of an extrapolated or evolved condition, virtual patient 130 may have become gravely ill, the symptoms may have exaggerated and potentially virtual patient 130 may have died as a result of the participant's actions or inaction. In such a case, the states of virtual patient 50, 90, and 130 corresponding EMR 60, 100, 140 may prove to be a valuable learning tool for the participant even in the presence of an undesirable outcome. Indeed, such a case may prove to be most beneficial and useful to a participant in teaching what not to do. Conversely, the various evolved states of the first virtual patient 30, 70, 110 may have progressed in a beneficial path such that the original conditions and problems have been completely resolved. Such a scenario and the associated EMR 40, 80, 120 may also prove to be a very valuable and useful learning tool for a participant. Indeed, even a medical-education implementation of a no-win scenario, or Kobayashi Maru, may be provided where no beneficial outcome is possible—yet, the participant's responses and manner of dealing with such a scenario may be captured, evaluated, and used to educate.

In the case of a series of subsequent encounters such series may continue indefinitely or may be terminated at any point. At any point in such a scenario, an instructor or evaluator may grade or evaluate the participant based on a plurality of factors such as the changing condition of the corresponding virtual patient, the responsive additions to the EMR, actions taken by the participant, or even simply evaluated according to a checklist of standard actions, responses, and/or tests to be ordered. Alternatively, as seen in FIG. 1, the beneficial outcome for virtual patient 110 may be graded relative to a bad outcome occasioned upon virtual patient 130. In such a manner, each individual participant may not be graded in accordance with a strict absolute scale, but rather, relative to the performance of their peers. Such a relative grading also has the advantage of providing a plurality of different inputs and treatment processes by a plurality of educated participants.

Figure 2:
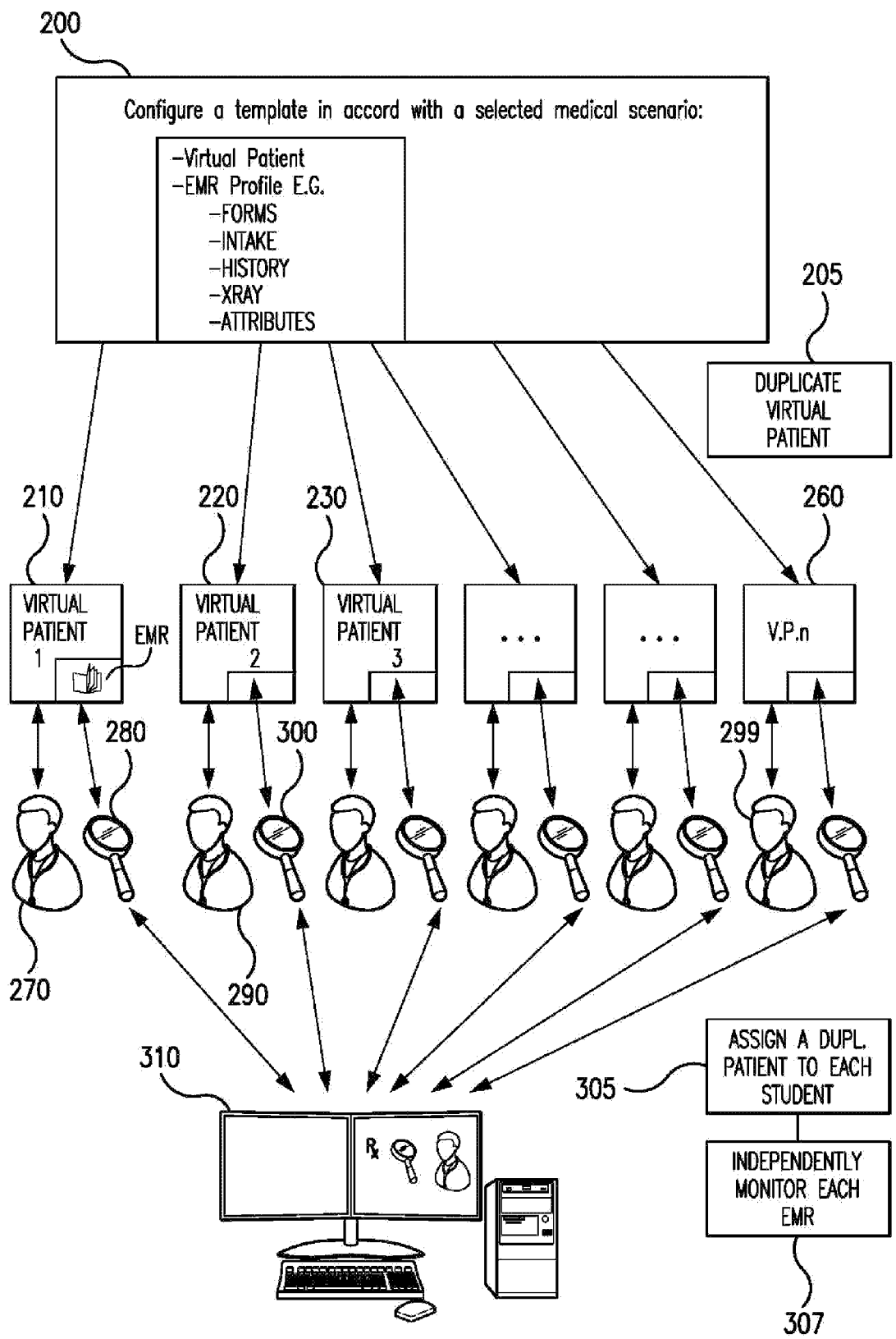
FIG. 2 is a flow diagram of a method of interactive simulation and evaluation in accordance with another exemplary embodiment of the present invention.

FIG. 2 is another simplified flow diagram of a method of interactive education, simulation, and evaluation involving electronic medical records (EMR) for a plurality of duplicated virtual patients. At step 200, a medical scenario (such as diabetes, pancreatic cancer, high blood pressure) is configured by selecting a plurality of forms which may be EMR items when they have been filled out and attached to or associated with an EMR. The scenario may include a virtual patient, an EMR profile for the virtual patient including forms, intake, history, potentially relics or artifacts (such as X-ray images, CAT scan images, MRI data), and attributes of the virtual patient such as height and weight.

At step 205, the configured virtual patient in accord with the selected scenario is effectively cloned by duplicating the EMR. One copy of the virtual patient is cloned for each participant. The virtual patient$_1$ 210 is duplicated for a participant 270. Virtual patient$_1$ 210 has an electronic medical record (EMR) associated with, relating to, or chronicling virtual patient$_1$ and their medical history. EMR$_1$ corresponds to virtual patient$_1$ and is provided with virtual patient$_1$ to participant 270. The virtual patient$_1$ 210 and the corresponding EMR are available both to the student 270 and to an evaluator 280 which may be an instructor, professor, or other evaluator of participant performance.

A plurality of other clones of the original virtual patient are provided including: virtual patient$_2$ 220, virtual patient$_3$ 230 . . . virtual patient$_n$ 260. Each of the virtual patients$_{1 \ldots n}$ are provided to a respective participant 270, 290 . . . 299. Each of the duplicated virtual patients 210, 220, 230 . . . 260, are provided to a respective participant 270, 290, 300 . . . 299.

At step 307, the EMRs of each of the virtual patients are separately and independently monitored such that additions to the EMR by the participants 270, 290 . . . 299, are independently tracked and maintained. At step 310, an evaluator is able to view and interact with each of the virtual patients 210, 220, 230, 260 and view the EMR associated with each individual virtual patient, the responsive additions of the students 270, 290, and 299, tests ordered, actions of the students 270, 290, 299, and their evaluations of the virtual patients 210, 220, 230, 260.

At an evaluation stage, step 310, one or a plurality of evaluators may evaluate and grade the performance of the participants 270, 290, 299. An absolute grading system, potentially based on a comparison between the participant's responsive actions relative to a set of idealized states, a checklist, or other suitable benchmark may be employed. Alternatively, each of the participants may be graded relative to a composite of the other participants' evaluations and/or responsive actions.

Figure 3:
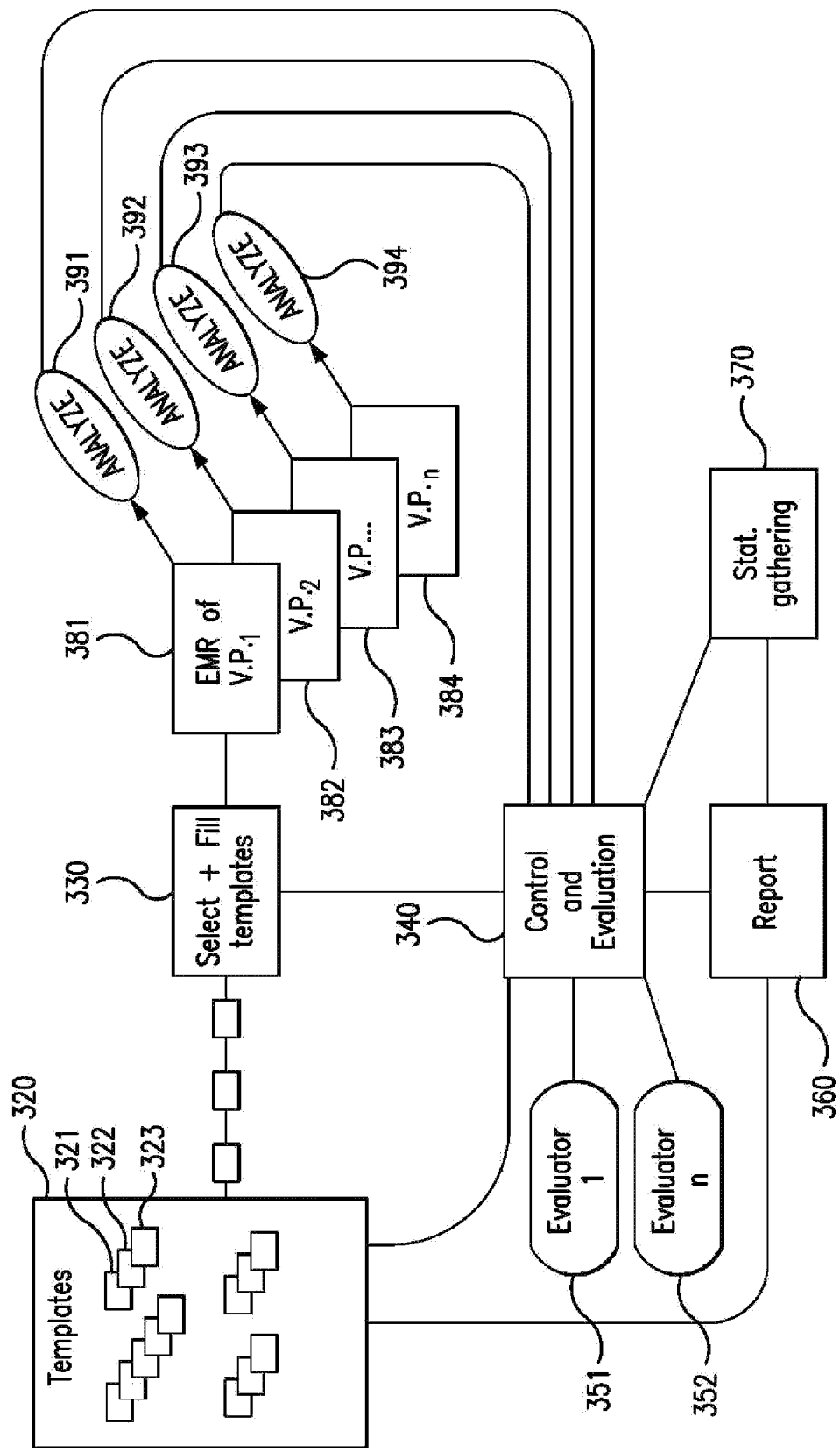
FIG. 3 is a simplified schematic diagram of the system for interactive simulation and evaluation in accordance with another exemplary embodiment of the present invention.

FIG. 3 is a simplified schematic of a system of interactive simulation and evaluation of clinical care for a plurality of duplicated virtual patients. FIG. 3 shows a template database or data store 320 of individual templates 321, 322, 323, EMR items, entire EMR folders, forms, data relics, artifacts, test results, multimedia, and the like. A template is defined as a building block for a form; a template may have a defined structure, but may be missing customization (e.g. Harvard Medical logo, specific EMR layout). Once a template has been configured for a specific establishment, the template will be a form. The template database 320 may be a relational database or any database known to one of skill in the art suitable to efficiently store and facilitate retrieval of such EMR items. Forms may be stored in a portable document format (PDF), tagged image file format (TIFF), portable network graphic (PNG), bitmap image file format (BMP), or, to enable fill-able forms, an extensible markup language (XML) may be employed with Microsoft Office INFOPATH® being used to design and modify forms.

To aid in efficiency, an entire form may be saved as a field in the database rather than processing each item or field in a form and storing these separately in the database. The templates stored in a template database or data store 320 are able to be selectively included in a scenario being established by an evaluator. The forms are selected and at least a portion of the forms are filled out at 330. Once the selected and filled out forms have been established, the EMR of the virtual patient is duplicated to effectively clone the virtual patient. The cloned virtual patients 381, 382, 383, and 384 are then provided—one to each participant. Each participant then analyzes one of a plurality of EMRs 391, 392, 393, and 394. An entire virtual patient (including their EMR) may be duplicated and assigned, or merely the EMR may be duplicated and assigned to each participant (depending on the selected scenario). Preferably, each participant employs in this regard a participant's station (which may be dedicated or otherwise shared with one or more other participants) implemented by any suitable means known in the art to provide the necessary software and/or hardware resources for establishing sufficient interactive user interface with other parts of the system.

The analysis, notes, responsive additions, tests required, results, and the like, are all independently and separately tracked, captured, and maintained by a control and evaluation module 340. The control and evaluation module 340 may indeed feed-back captured data from participants into the template database or data store 320. Doing so may provide for an ongoing/persistent virtual patient, with a corresponding EMR such that participants are able to have subsequent encounters/scenarios, responsive additions, and evaluations of the virtual patient. Also it may be the case that an evaluator finds a student or a participant's response to be particularly beneficial in furthering other student's learning and may therefore save the virtual patient and/or accompanying EMR into the template database 320 to be able to be used for further instruction in another scenario.

An evaluator 351 or evaluator$_n$ 352 may interact with the control and evaluation module 340 to review participant additions, actions, and results. This interaction is preferably realized through an evaluator's station implemented by any suitable means known in the art to provide the necessary software and/or hardware resources for establishing sufficient interactive user interface with such other parts of the system. The evaluators 351, 352 may employ control and evaluation module 340 to generate a report 360. The generated report 360 may be a broad report covering the plurality of participants' responses to the EMR and their respective virtual patients or the report may be more granular by covering an individual participant and individual actions or responses by that participant to the provided stimulus. Such a report 360 may include any data generated or incorporated in the entire process. Such a report may indeed include video of the patient encounter (even potentially from a plurality of different angles within an encounter room). Still further, the report 360 may include detailed notes, patient feedback, charts, test results, checklists filled out by an evaluator, a component of peer grading or evaluation from co-participants, or the like. The control and evaluation module 340 also may be employed to harvest data from an individual participant, a plurality of participants, or the entirety of all the participants. Such data gathered may then be analyzed statistically to arrive at any number of different measurements such as educational effectiveness, rate/severity of mistakes, and the like.

Figure 4:
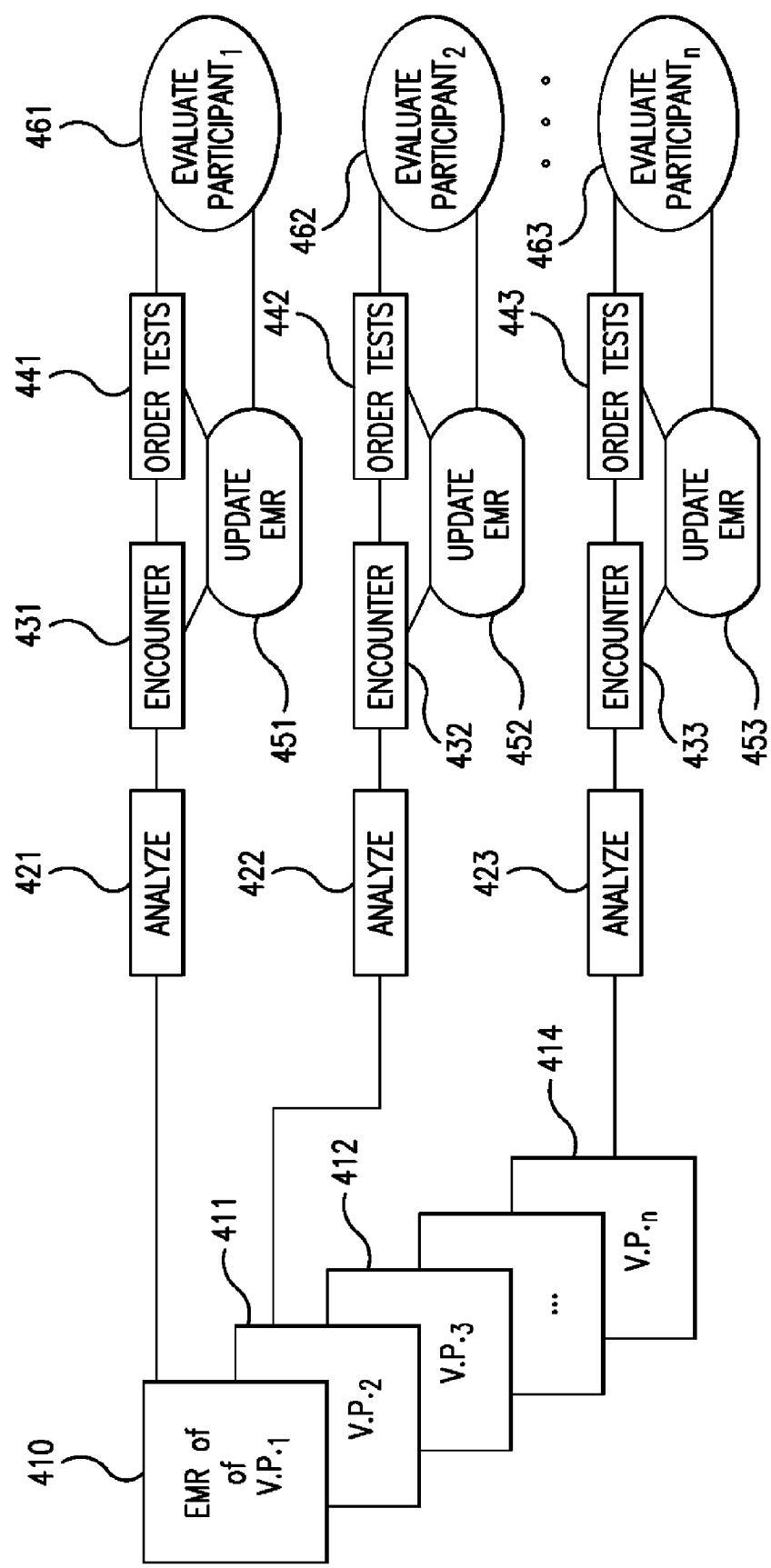
FIG. 4 is a flow diagram of a method of simulation and evaluation in accordance with another exemplary embodiment of the present invention.

FIG. 4 is another simplified flow diagram of a method of interactive education for maintaining electronic medical records (EMRs) for a plurality of duplicated virtual patients. Initially, a plurality of EMRs for corresponding cloned virtual patients are provided 410, 411, 412 . . . 414. The plurality of EMRs correspond to a plurality of virtual patients: virtual patient$_1$, virtual patient$_2$, virtual patient$_3$ . . . virtual patient$_n$. Each of the individual EMRs for each individual virtual patient are independently tracked, maintained, and analyzed by participants.

For example, the EMR of virtual patient$_1$ 410 is analyzed at step 421 by a first participant; such an analysis may indeed be a pre-encounter analysis. An evaluator may selectively enable the participant to be able to analyze the EMR 410 of the virtual patient$_1$ prior to an encounter 431 with such a virtual patient (represented by a computer generated simulation, a real-world interaction with an actor portraying a virtual patient, or a manikin). Such an encounter may be something as simple as a nurse filling in an intake form for a new patient. However, such an encounter may be something as complicated as an appendectomy performed on a manikin patient.

Illustratively, the participant may order tests 441 responsive to the patient's history, the analyzed EMR, or indicia that a virtual patient, actor, or manikin may display or exhibit. Throughout the encounter, the participant may update EMR 451 responsive to notes, preliminary diagnoses, and indicia of interest.

Either once the encounter is complete, or in an ongoing-evaluation, the participant) is evaluated at step 461 based at least in part upon the tests ordered at step 441 and the updates to the patient's EMR at step 451. Similarly, a second EMR 411 of virtual patient$_2$ may be assigned to a second participant and analyzed by the second participant at step 422. The second participant may have a separate and distinct encounter 432 where tests are ordered at step 442, and the EMR is updated at step 452. The evaluator may then evaluate participant$_2$ at step 462 based on that particular participant$_2$'s encounter 432, analysis 422, tests ordered, or responsive actions 442, and updates to the EMR performed by that participant 452.

A participant$_n$ may be provided with the virtual patient and corresponding EMR$_n$ 414 where that participant$_n$ analyzes 423, encounters 433, orders tests 443, performs other responsive actions, updates the EMR of virtual patient$_n$ 453, and participant$_n$ is evaluated at 463 responsive to the EMR$_n$ and virtual patient$_n$.

Inasmuch as the interactive educational simulation may be concurrently provided to a plurality of students, provision of a scheduling component, operable to perform logistical coordination of manikins, actors, simulation rooms, necessary medical equipment, infrastructure related to capture of the participant's performance, as well as participant schedules and requirements may be provided. The functional features illustrated in FIGS. 4 and 5, including features 330, 340, 360, 370, and 421-463 may be implemented in one or more selectively executable control modules of a computer-processor based simulation management unit.

Figure 5:
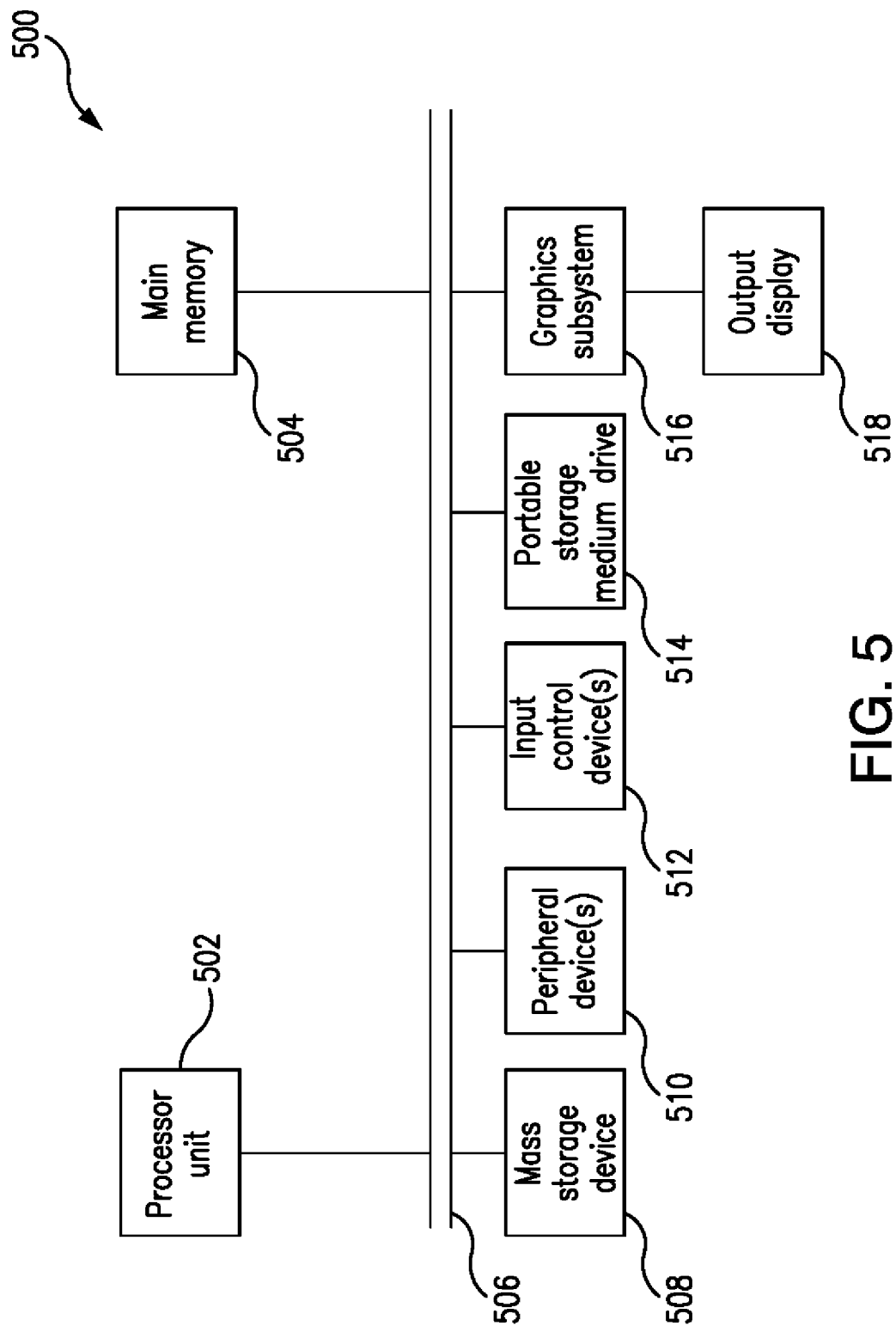
FIG. 5 is a schematic diagram of a system in accordance with another exemplary embodiment of the present invention.

FIG. 5 illustrates a block diagram of a computer system for interactive education simulation and evaluation for clinical care of a plurality of virtual patients in accordance with various embodiments of the present invention. A computer system 500 contains a processor unit 502, a main memory 504, an interconnect bus 506, a mass storage device 508, peripheral device(s) 510, input control device(s) 512, portable storage drive(s) 514, a graphics subsystem 516, and an output display 518. Processor unit 502 may include a single microprocessor or a plurality of microprocessors for configuring computer system 500 as a multi-processor system. Main memory 504 stores, in part, instructions and data to be executed by processor 502. Main memory 504 preferably includes banks of dynamic random access memory (DRAM) as well as high-speed cache memory.

For the purpose of simplicity, the components of computer system 500 are connected via interconnect bus 506. However, computer system 500 may be connected through one or more data transport measures. For example, processor unit 502 and main memory 504 may be connected via a local microprocessor bus and mass storage device 508, peripheral device(s) 510, portable storage medium drive(s) 514, and graphic subsystem 516 may be connected via one or more input/output (I/O) buses. Mass storage device 508, which may be implemented with a magnetic disk drive, an optical disk drive, a solid state device, or an attachment to network storage, is a non-volatile storage device for storing data, databases, and instructions, to be used by processor unit 502. In a software embodiment, mass storage device 508 may store the software to load it into main memory 504.

Portable storage medium drive 514 operates in conjunction with a portable non-volatile storage medium such as a floppy disk, a compact disk read only memory (CD-ROM), or a digital versatile disk read only memory (DVD-ROM), to input and output data and code to and from the computer system 500. In one embodiment, the software is stored on such a portable medium, and is input to computer system 500 via portable storage medium drive 514. Peripheral device(s) 510 may include any type of computer support device such as an input/output (I/O) interface, to add additional functionality to computer system 500. For example, peripheral device(s) 510 may include a network interface card to interface computer system 500 to a network.

Input control device(s) 512 provide a portion of the user interface for a computer system 500. Input control device(s) 512 may include an alphanumeric keypad for inputting alphanumeric and other key information; and a cursor control device such as a mouse, a track pad or stylus; or cursor direction keys.

In order to display textual and graphical information, computer system 500 contains graphic subsystem 514 and output display(s) 518. Output display 518 may include a cathode ray tube (CRT) display, liquid crystal display (LCD), plasma, projector, or active matrix organic light emitting diode (AMOLED) display. Graphic subsystem 516 receives textual and graphical information and processes the information for output to display 518.

In a software implementation, the interactive simulation software includes a plurality of computer executable instructions, to be implemented on a computer system. Prior to loading in the computer system, the interactive simulation software may reside as encoded information on a computer-readable tangible medium such as a magnetic floppy disk, a magnetic tape, CD-ROM, DVD-ROM, flash memory, or any other suitable computer readable medium.

Figure 6:
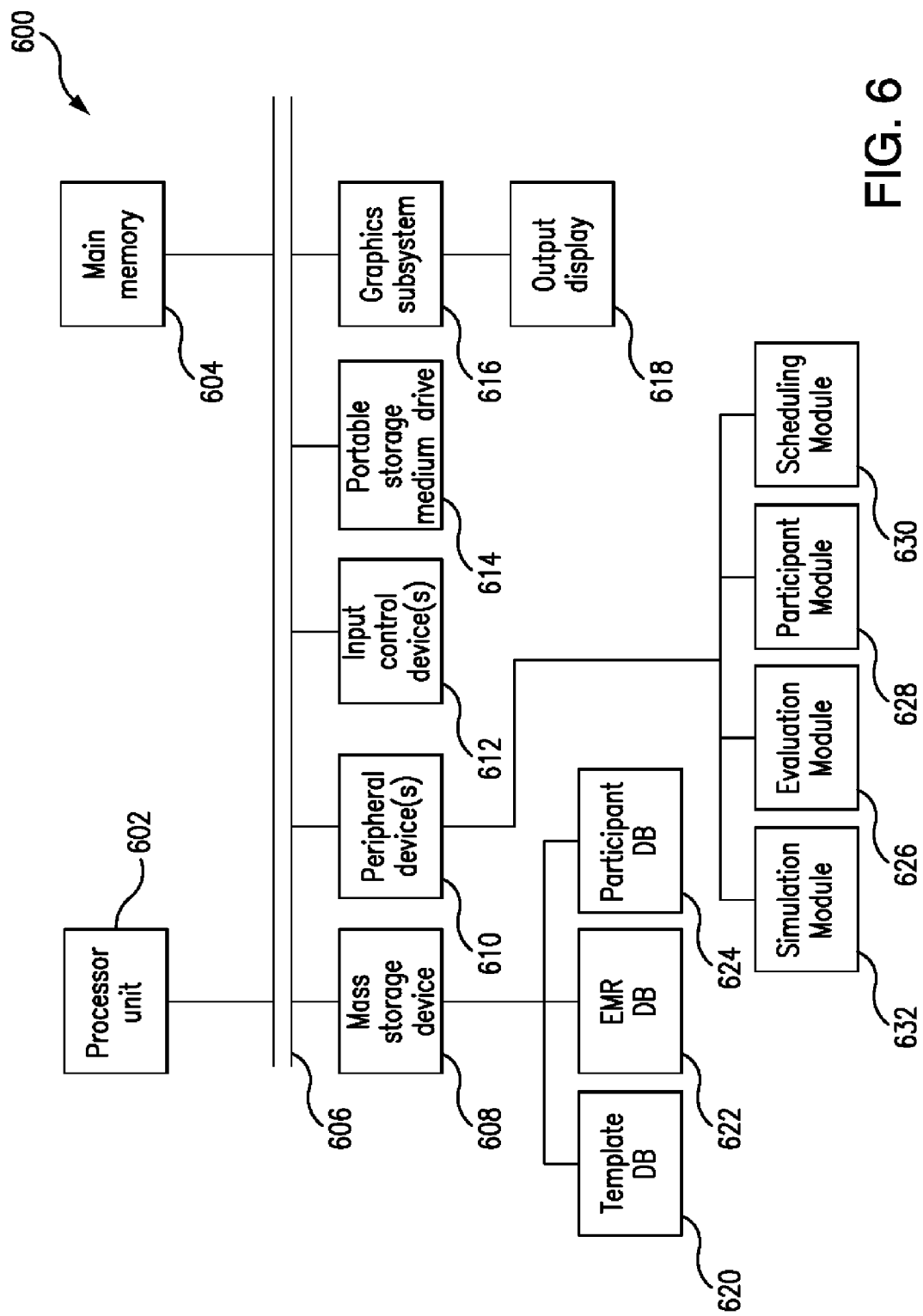
FIG. 6 is another simplified schematic diagram of the system in accordance with another exemplary embodiment of the present invention.

In a hardware implementation, such a system may be implemented in any suitable computer based platform known in the art. For example, the system may comprise suitable storage media and one or more dedicated processors or share one or more processors executing/controlling other functions, wherein the employed processor(s) is programmably configured with processor instructions for performing the functions described herein. Suitable circuits may also be developed to execute certain aspects of these functions. FIG. 6 shows one such exemplary hardware implementation.

FIG. 6 is another simplified schematic of a system of interactive education, simulation, and evaluation in accord with an embodiment of the present invention. FIG. 6 illustrates a block diagram of a computer system for executing interactive education simulation in accordance with various embodiments of the present invention. A computer system 600 contains a processor unit 602, a main memory 604, an interconnect bus 606, a mass storage device 608 (which may include, for example, template/forms 620, virtual patient 622, participant 624 databases (DB)), peripheral device(s) 610, input control device(s) 612, portable storage drive(s) 614, a graphics subsystem 616, and an output display 618.

Main memory 604 stores, in part, instructions and data to be executed by processor 602. For the purpose of simplicity, the components of computer system 600 are connected via interconnect bus 606. Peripheral device(s) 610 may include an evaluation module 626 operable to evaluate participant responses\updates to EMR, participant module 628 operable to independently track participants, scheduling module 630 operable to schedule access to resources and infrastructure, simulation module 632 operable to execute the simulation, and the like.

Input control device(s) 612 provide a portion of the user interface for a computer system 100 user. Input control device(s) 612 may include an alphanumeric keypad for inputting alphanumeric and other key information; and a cursor control device such as a mouse, a track pad or stylus; or cursor direction keys.

In order to display textual and graphical information, computer system 600 contains graphic subsystem 614 and output display(s) 618. Graphic subsystem 616 receives textual and graphical information and processes the information for output to display 618.

Figure 7:
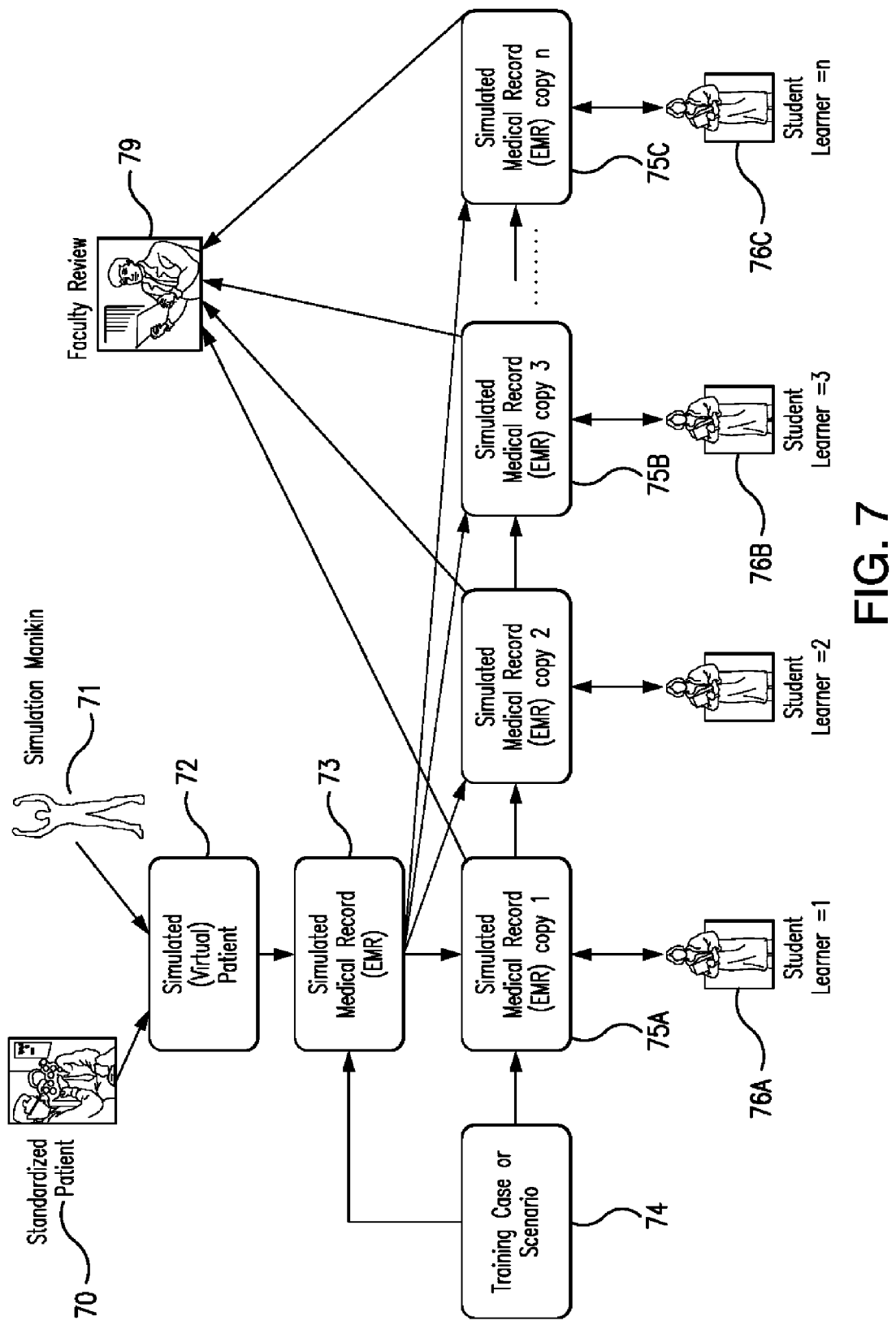
FIG. 7 is another simplified flow diagram of a method of interactive education in accord with another exemplary embodiment of the present invention.

FIG. 7 illustrates another simplified flow diagram of a method of interactive simulation, education, and evaluation of clinical care of a plurality of virtual patients. Initially a standardized patient 70 is established having attributes, symptoms, and indicia which comport with a predefined condition in-line with an evaluator's chosen scenario. Such standardized patient 70 may be embodied in a manikin 71, actor, or other such suitable prop. Throughout a scenario or case, an actor may be used for one portion and a manikin for another portion that would not be easily performed on an actor—such as an intubation procedure. Preferably, the standardized patient 70 will be standardized to present the same symptoms, history, answers to questions, and the like to enable an unbiased assessment of all students. A simulated virtual patient 72 may be established embodying the standardized patient 70 in EMR. In this embodiment, one EMR of the virtual patient 72 may be instantiated for each participant 76A, 76B, 76C thereby effectively cloning the virtual patient, each with a separate copy of the EMR 75A, 75B, 75C. Each EMR 75A, 75B, 75C and student additions/updates thereto will preferably be separately maintained. Upon completion of the training case or scenario 74, each EMR 75A, 75B, and 75C will undergo faculty review 79 by an evaluator.

Figure 8:
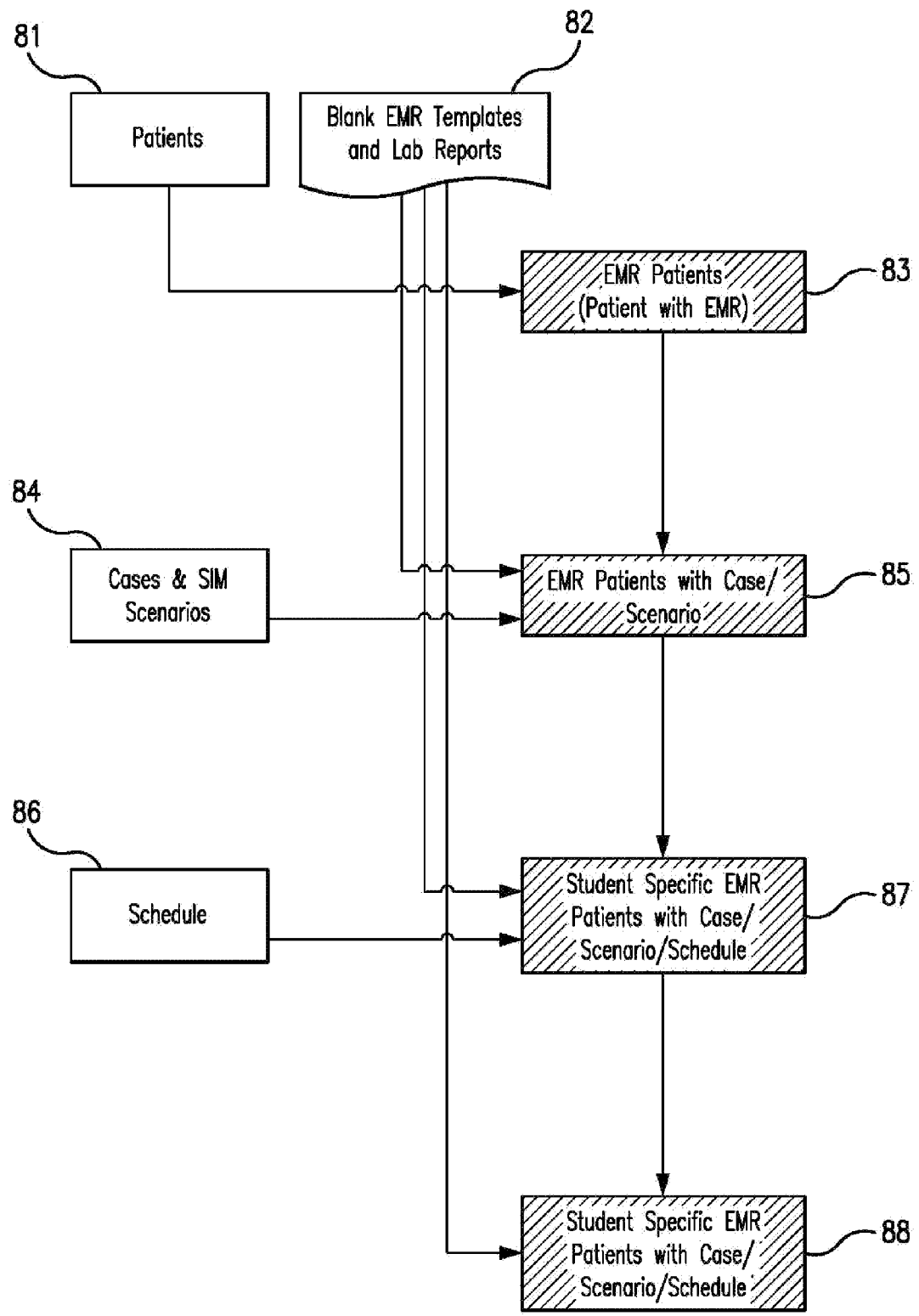
FIG. 8 is a simplified flow diagram of a method of building virtual patients having an associated EMR, scenario, and scheduling.

FIG. 8 illustrates a simplified flow diagram of a method for building and scheduling EMRs and simulations. A database or bank of patients 81 is maintained and a blank or partially established patient is drawn from the bank of patients 81. Such patients may be endowed with certain characteristics at step 83 which will prove particularly useful in the intended scenario or test-case to be simulated. Similarly, a database or bank of EMR items, including, for example: forms, lab reports 82, and the like are maintained and drawn from to establish EMRs to correspond to the established virtual patients. EMR patients may be associated with one or more cases and/or simulation (sim) scenarios 84 which may involve designating a target diagnosis, a medical task to be performed, and/or a checklist by which to evaluate the performance of tasks or making of diagnoses. The EMR patients within case/scenario 85 may then be assigned a specific schedule for the simulation to be run, co-participants, rooms, medical equipment, and the like to be reserved at step 86. The student specific EMR patients with case/scenario and schedule 87 may each be selectively provided to a particular student.

FIG. 9 shows an exemplary screen shot of a system for building EMRs for virtual patients in accord with the present invention. A selected virtual patient may have a plurality of attributes 91 that may be configurable to more closely match a selected scenario. For example, a patient's age, gender, weight, height may be suitably adjusted to indicate (in concert with other EMR items) that a certain diagnosis is likely.

A bank or database of EMR items 92 may be made available to an evaluator to selectively construct a particular EMR profile 94 to indicate the selected target diagnosis. EMR items may include, for example: assessments, logs, diaries, intake forms, and flows.

Figure 10:
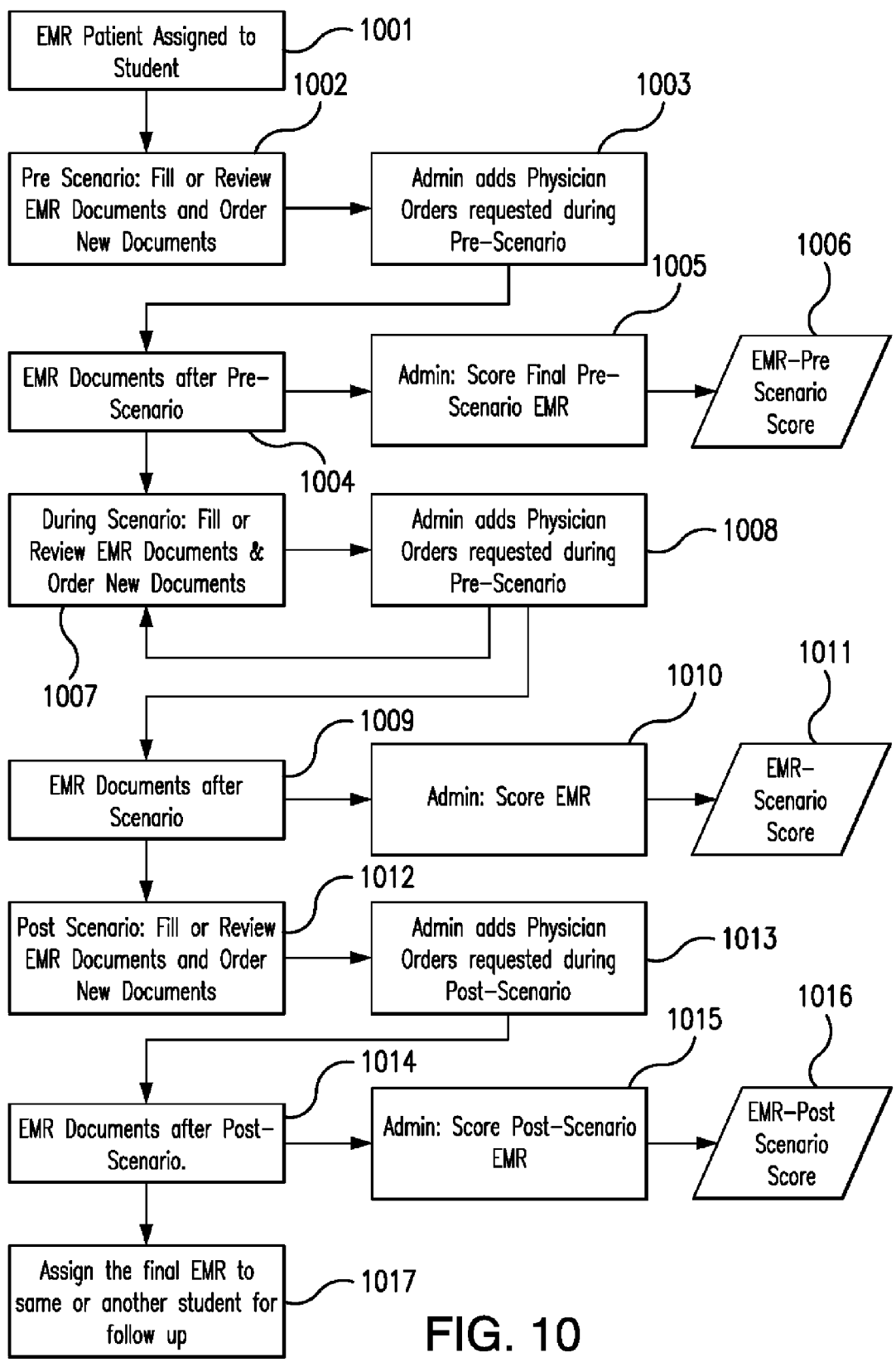
FIG. 10 is a simplified flow diagram of a method of interactive simulation and evaluation in accordance with an embodiment of the present invention.

FIG. 10 illustrates another exemplary flow diagram for an interactive educational simulation and grading in accord with another embodiment of the present invention. At step 1001 an instantiated EMR patient is assigned to a particular student. At step 1002, prior to an encounter or practical assessment, a student may be permitted to review existing EMR items or documents, make additions, update, or change certain portions of the EMR. The student may also be empowered to make orders to have additional tests performed, such as a blood test, CAT scan. At step 1003, an evaluator or administrator may add the orders and/or the results of the orders embodied in additional EMR items. At step 1004, the participant may again be permitted to view the EMR and/or make responsive additions to the EMR following the orders/tests being performed. Following step 1004, an evaluator may score the participant's actions at step 1005. Step 1006 may entail a reporting or indication of the score received at step 1005. Such reporting at step 1006 may provide constructive feedback to the student to improve future actions.

At step 1007, during the simulation, scenario, or encounter, the participant may again review the EMR and be permitted to make additional orders and/or update the EMR. At step 1008, an administrator may execute and incorporate results of the orders given by the participant into the EMR. Step 1008 may be performed after the encounter/simulation/scenario, or contemporaneously with live feedback and updating of the EMR. After the scenario has been completed, the EMR documents 1009 are then passed on to the administrator or other such evaluator where they are graded at step 1010 and a resultant score may then be reported at step 1011.

Following the scenario's completion, the participant may again be permitted to review, update, and add to the EMR, making responsive orders at step 1012 to be added by an administrator at step 1013. The EMR 1014 (post-scenario) will be fully incorporative of all tests ordered and additions by the participant by step 1015 where the EMR will be provided to the evaluator to be scored and reported at step 1016. Optionally, if the virtual patient clone has been established to be persistent, such patient may be maintained and revisited by the same or another student at step 1017 during a subsequent encounter or scenario.

Figure 11:
FIG. 11 is another exemplary screen shot of a system in accordance with an embodiment of the present invention.

FIG. 11 is an exemplary screen shot of a system in accordance with another embodiment of the present invention. It is seen that a virtual patient 1101 has been established and a plurality of different EMR items 1102 have been associated with the virtual patient 1101. A particular EMR item "Adult Assessment—Safety & Skin Care Activity" is being displayed as a form. A template stored in the database may be specifically configured to resemble an actual EMR form that will be in use at a particular facility where participants are likely to be employed or are already employed. The form may mirror and be substantially identical to actual forms used, including the layout, symbol or logo 1103, and particular fields 1104, 1105. Thereby a participant will be familiarized with actual forms used by a particular institution.

FIG. 12 is a simplified flow diagram of a method of simulating and evaluating clinical care of a plurality of virtual patients. At step 1201, an exemplary virtual patient "Steve Blake" is coupled with a blank template. The blank template may be customized to the scenario selected by an evaluator—including customization for the procedure to be performed and the institution where the procedure is to be performed. Additionally, further templates 1202, evaluations 1203, virtual patients 1204, access permissions 1205, date 1206, Exam/Training Information 1207, Student (Role) information 1208, Case information 1209, and history 1210 may all be combined to establish a new form for the virtual patient. Once established at step 1211, a first instance of the virtual patient may have new auxiliary information added such as new vitals 1212A or patient notes 1213A. Such auxiliary information added to the first instance of the virtual patient will be maintained separately from a separate virtual patient instance (or clone). In, for example, a second instance of the virtual patient, vitals 1212B and patient notes 1213B may be separately maintained from the first instance.

Figure 13A:
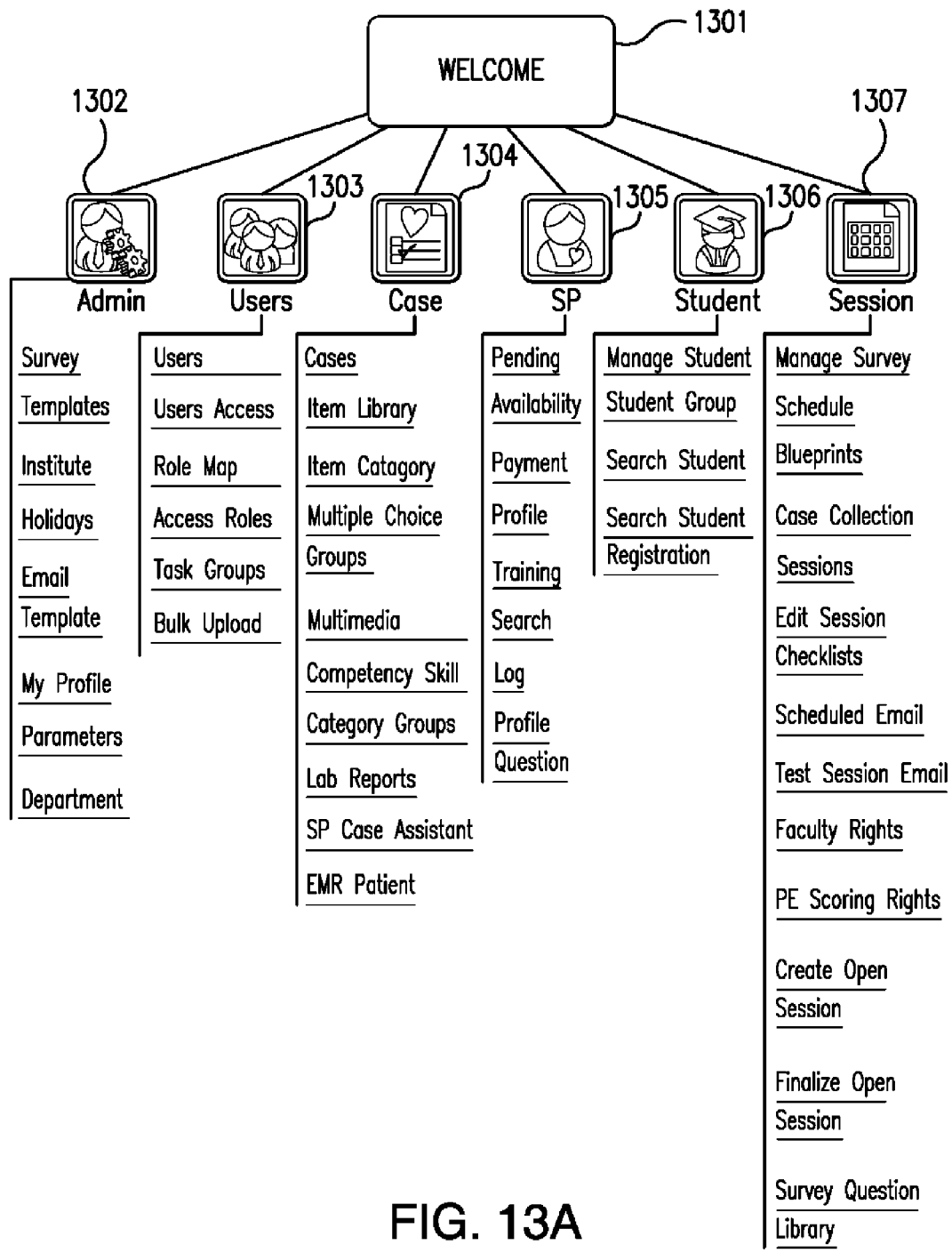
FIGS. 13A and 13B are simplified schematic diagrams of a system in accordance with an embodiment of the present invention.
Figure 13B:
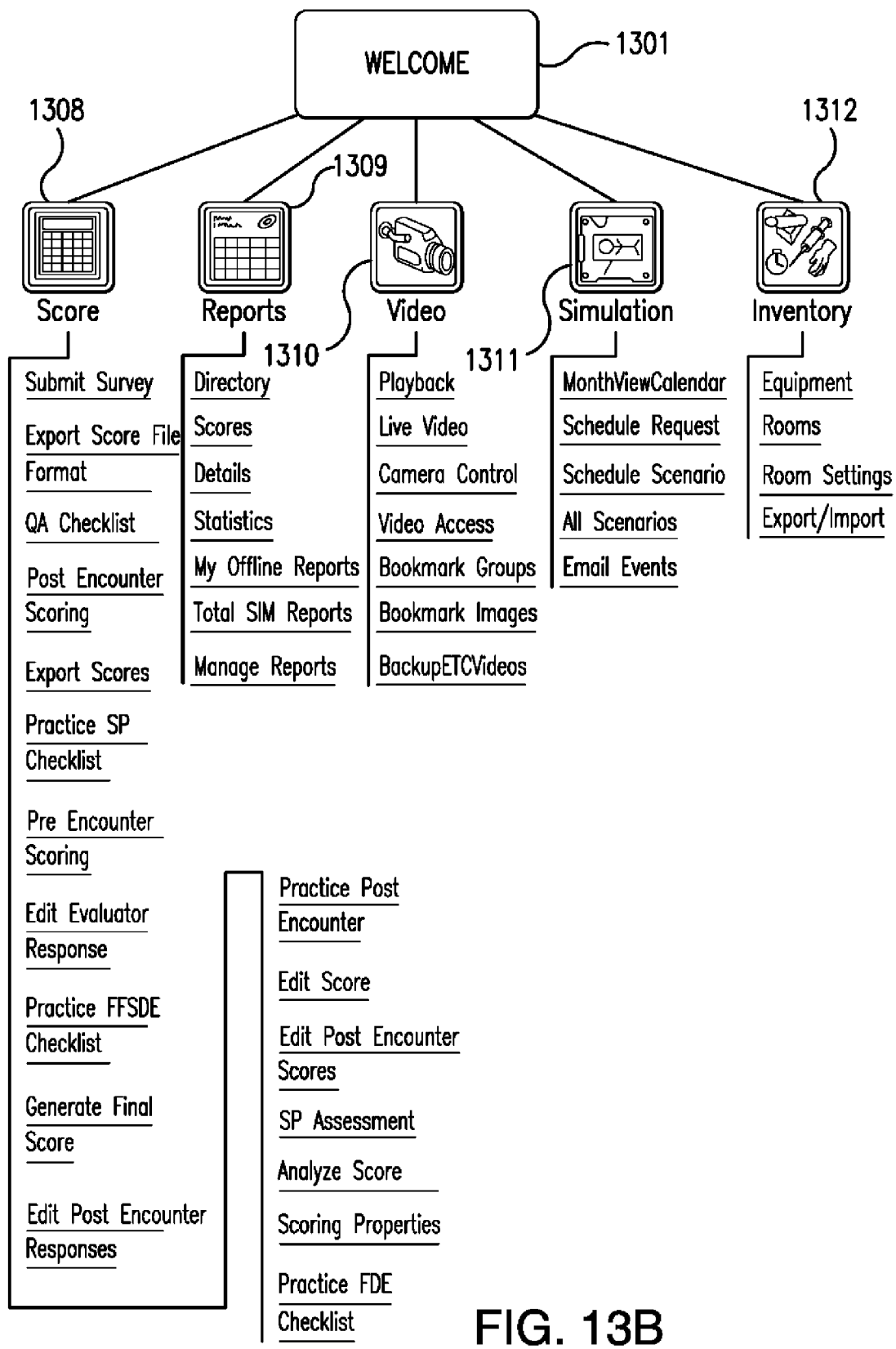

FIGS. 13A and 13B are simplified schematic diagrams of a system of interactive education in accord with one embodiment of the present invention. A welcome module 1301 provides a unified user interface enabling a user to interact with the plurality of system modules 1302-1312. The system includes an Admin module 1302 (operable to perform administrative tasks such as template building, institute specific forms customization and the like). A User's module 1303 provides for tasks such as user access customizations, roles, groups, and the like. A Case module 1304 is operable to view and modify clusters of pre-selected EMRs to accompany a specific scenario or case. SP module 1305 is operable to view actors' pending scenarios/cases, schedule availability, training, and the like. Student module 1306 provides for student related functions, such as management of students, group forming. Session module 1307 is operable to email students, establish surveys, and the like. Score module 1308 provides for scoring functions, such as survey submission, various scoring functions, checklists. Reports module 1309 may provide for statistical composite analysis and reporting, individual grade reporting, records management, and similar types of functions. Video module 1310 allows for the managing of multiple-camera-recording encounters, historical recorded videos, bookmarking of videos and images, and other video-based tasks. Simulation module 1311 provides for management of simulation tasks such as scenario schedules, calendaring functions, and general simulation management. Inventory module 1312 allows for the management of inventory items such as manikins, medical equipment, auxiliary equipment used for simulations, and rooms.

Figure 14:
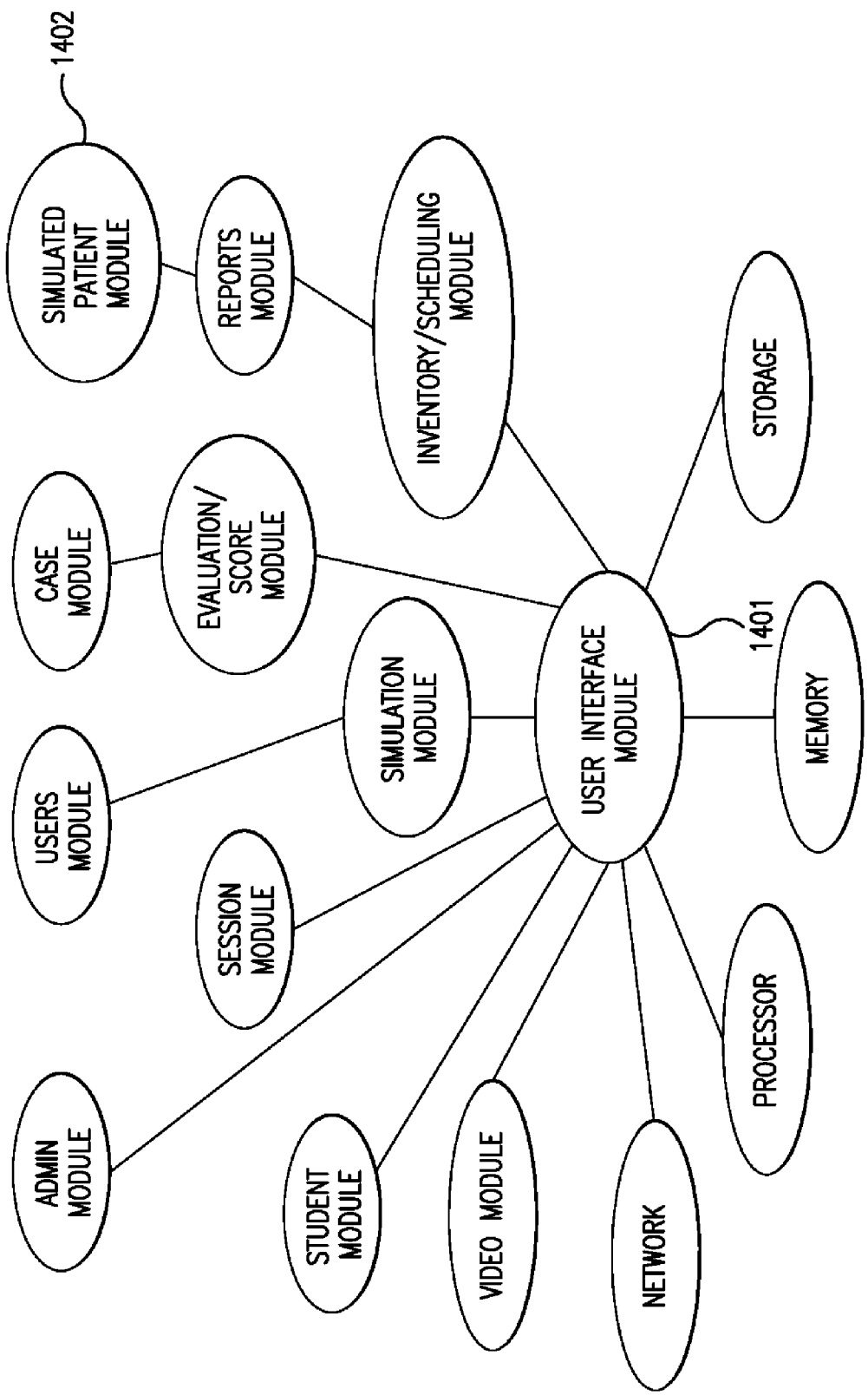
FIG. 14 is a simplified schematic diagram of a system in accordance with an embodiment of the present invention.

FIG. 14 is another simplified schematic of a system of interactive education in accord with one embodiment of the present invention. FIG. 14 shows a plurality of functional modules (such as a simulated patient module 1402 and a user interface module 1401) interfacing with a processor, memory, storage, and a network interface.

Figure 15:

FIG. 15 shows an exemplary screen shot of a system of interactive education in accord with an embodiment of the present invention. A system may provide a main menu function 1501 where related categories of features may be grouped for easy access by a user. In the instant main menu 1501, functionally related groups include: Admin, Users, Case, SP, Student, Session, Score, Reports, Video, Simulation, and Inventory—though the functional groups may be arranged differently, and may include more or less groups.

Figure 16:
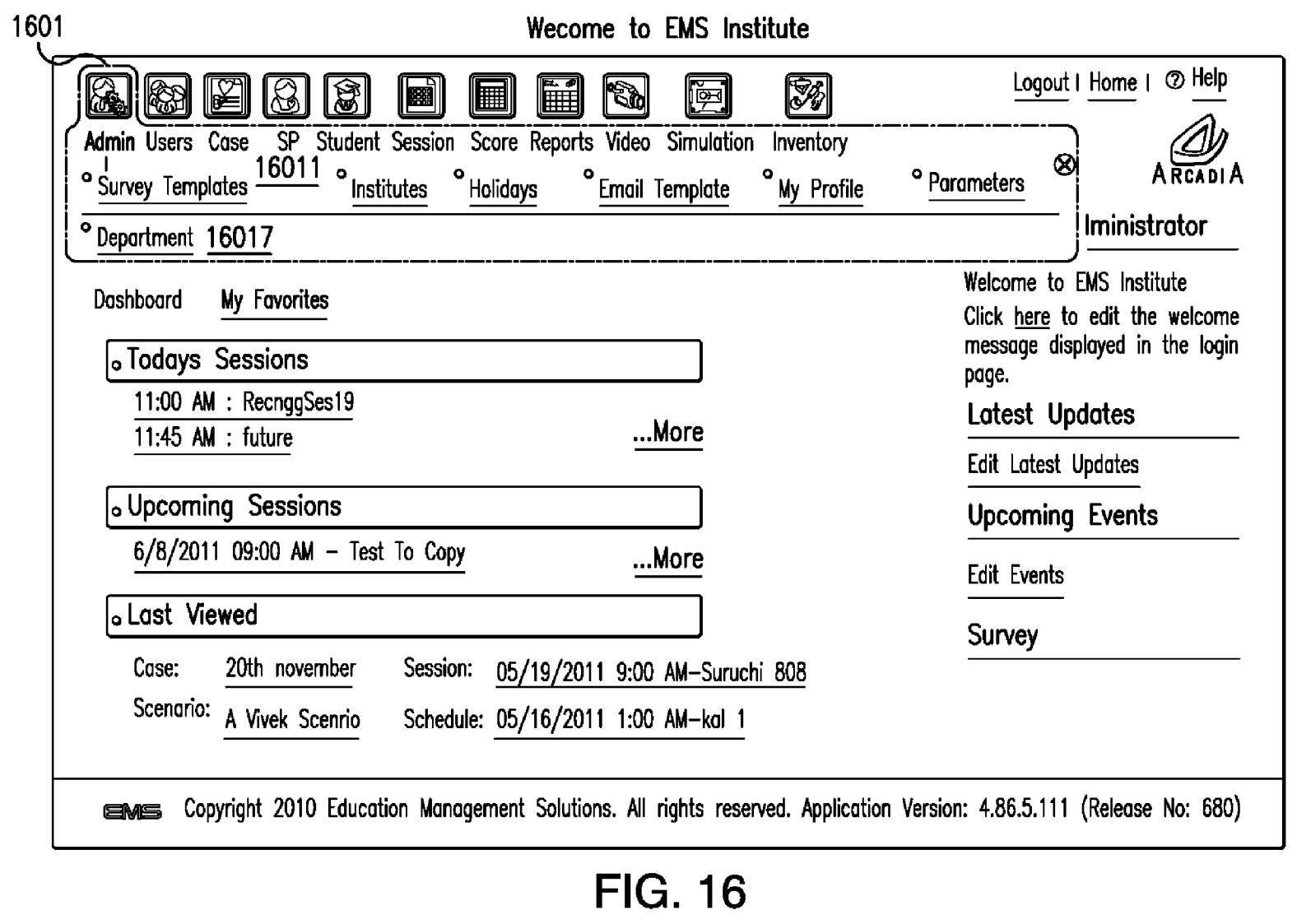

FIG. 16 shows an exemplary screen shot of an interaction with a first functional group in the main menu. Here, the Admin group 1601 has been accessed and a multitude of tasks being related to Admin functions have been displayed. Such tasks in the Admin group 1601 may include, for example: a survey templates task 16011 and a Department task 16017 along with other tasks related to the Admin group 1601.

Figure 17:
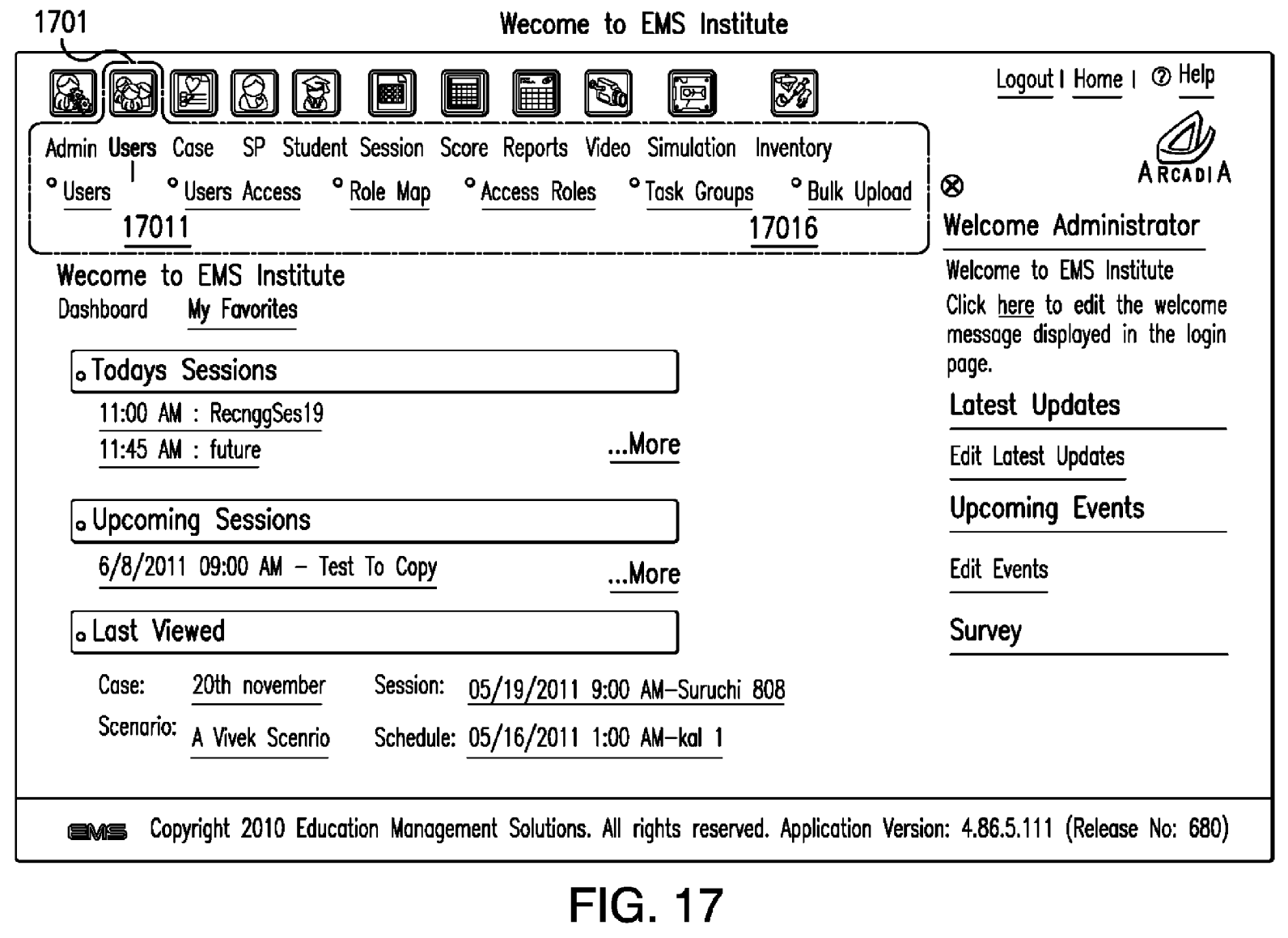

FIG. 17 shows another exemplary screen shot of an interaction with a second function group in the main menu. User's group 1701 has been opened—revealing tasks associated with or related to the User's group. For example, User's task 17011 may allow an administrator to configure different users for the system. Another exemplary task displayed is the Bulk Upload task 17016 which may allow for a batch upload of users without requiring particularized configuration.

FIG. 18 shows an interaction with the Case group 1801 providing tasks related to cases such as: Cases 18011, which may allow for configuration of different cases, and EMR Patient 18020, which may provide for management of previously configured virtual patients and their respective EMRs.

FIG. 19 shows an interaction with the SP group 1901 providing tasks related to SP (Simulated Patients). Such tasks may include managing Pending 19011 scenarios that an SP is allocated to or managing Profile Questions 19018, among other tasks.

Figure 20:
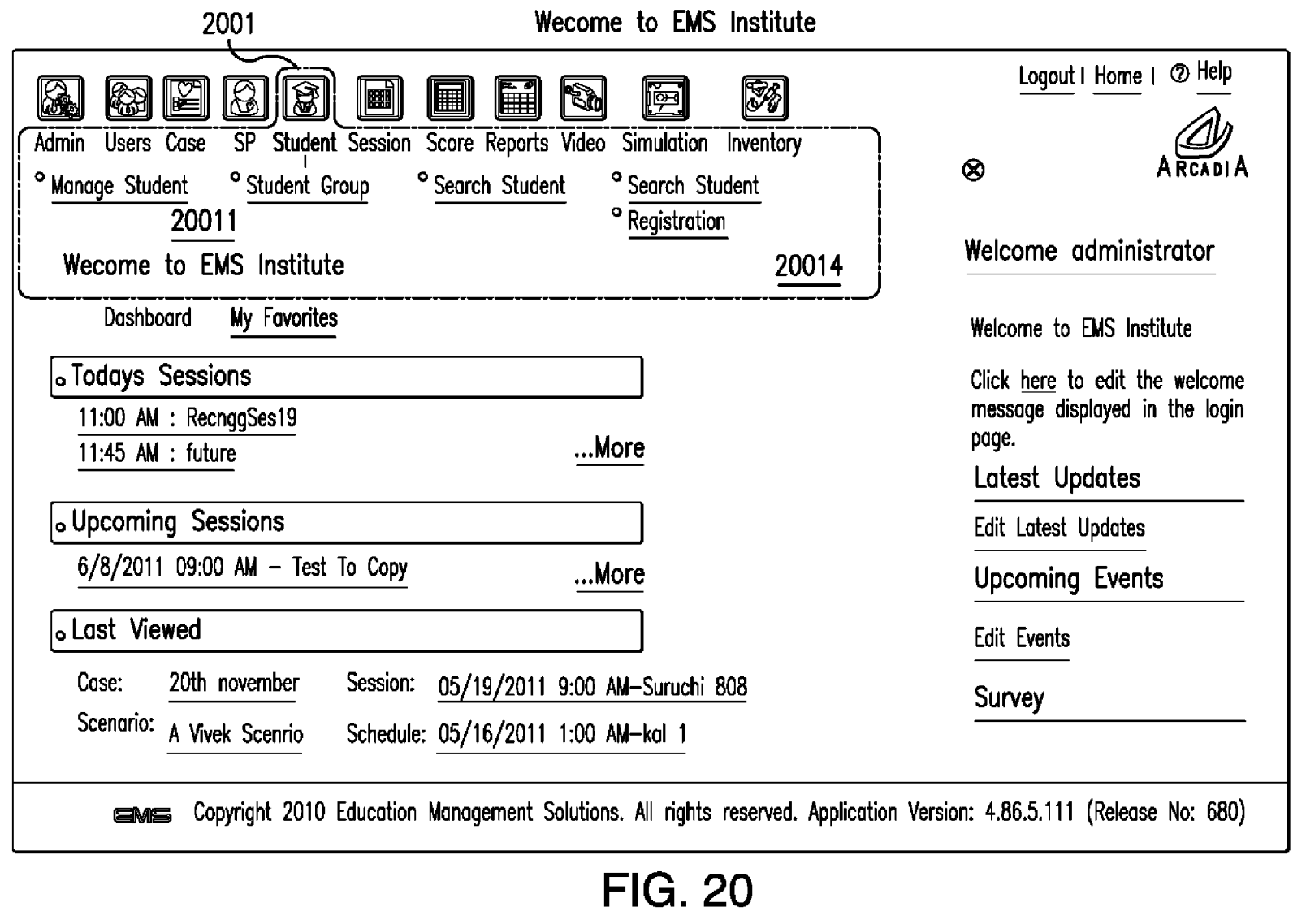

FIG. 20 shows an engagement of an exemplary Student group 2001, displaying tasks related to the student group, such as Manage Student 20011 and Search Student Registration 20014.

Figure 21:

FIG. 21 illustrates a multitude of different tasks related to Session management. Included in the Session group 2100 are tasks such as: Manage Survey Schedule 21001 and Survey Library Questions 21002.

Figure 22:
Figure 23:
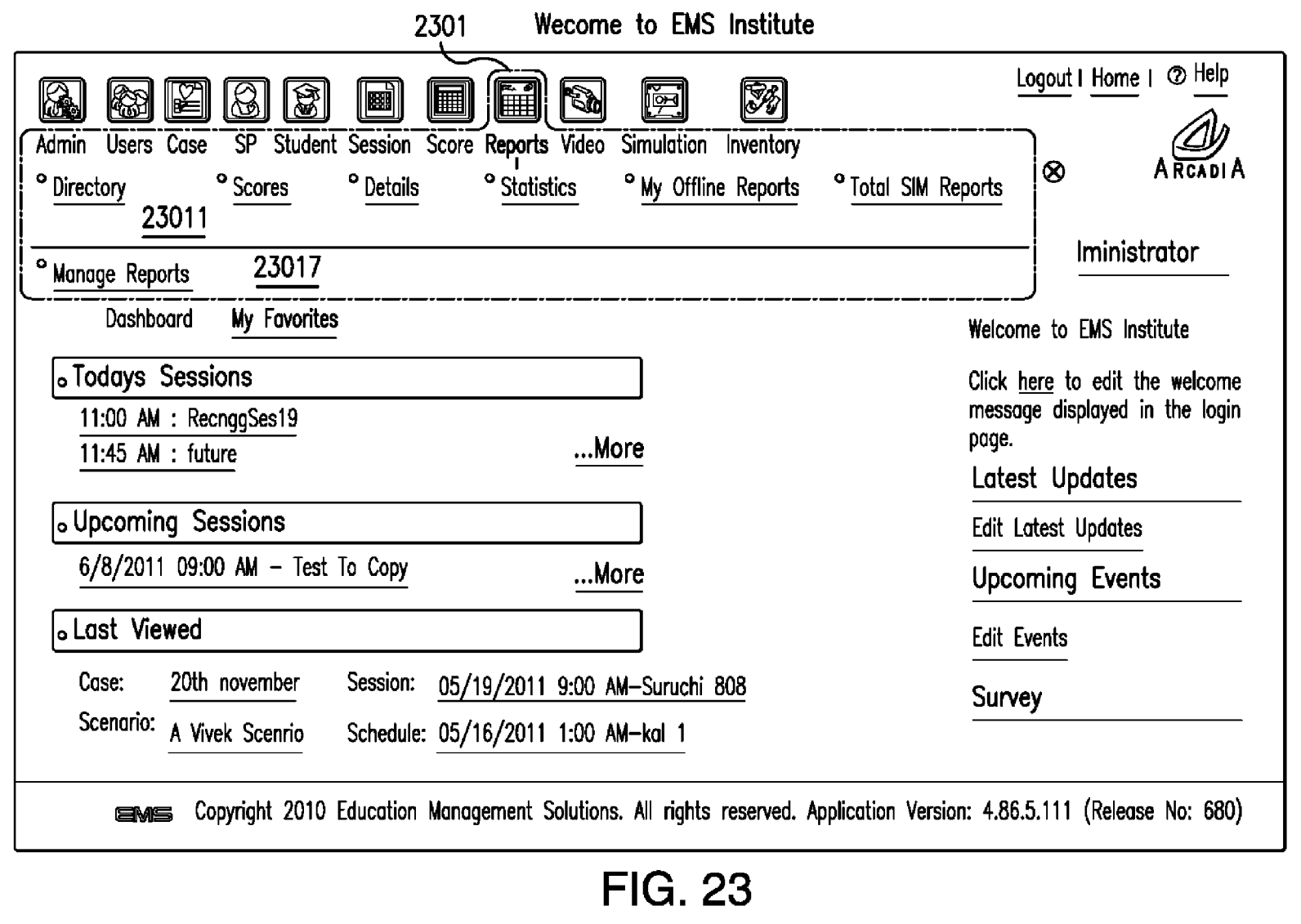

FIG. 22 shows the Score group 2201, including several exemplary tasks related to scoring, including, for example: Submit Survey 22011 and Practice FDE Checklist 22028, among other tasks. FIG. 23 illustratively shows the Reports group 2301 including a Directory task 23011 and a Manage Reports 23017 task, among other tasks. FIG. 24 shows a Video group 2401 including the related tasks: Playback 24011 and BackupETCVideos 24017. FIG. 25 shows an exemplary Simulation group 2501 and includes MonthViewCalendar 25011 and Email Events 25015. FIG. 26 shows an exemplary activation of the Inventory group 2601. The Inventory group may contain tasks such as: Equipment 26011 (item number and export/import).

Thereby, a designer with minimal effort, expended time, and reduced costs may establish an automated system and method for interactive simulation and evaluation of clinical care for a plurality of virtual patients.

Although this invention has been described in connection with specific forms and embodiments thereof, it will be appreciated that various modifications other than those discussed above may be resorted to without departure from the spirit or scope of the invention. For example, equivalent elements may be substituted for those specifically shown and described, certain features may be used independently of other features, and in certain cases, particular combinations of circuit design and implementation flows or processing steps may be reversed, interposed, or combined, all without departing from the spirit or scope of the invention as defined in the appended Claims.

What is claimed is:

1. An interactive evaluation system for simulating clinical care of a virtual patient comprising:
    a database of electronic medical records, at least one said electronic medical record (EMR) including a plurality of EMR items collectively profiling the virtual patient;
    a simulation management unit coupled to said database, said simulation management unit including a plurality of selectively executable control modules;
        at least a first of said control modules being executable to define a simulation scenario with respect to the virtual patient;
        at least a second of said control modules being executable to generate a plurality of clones of the virtual patient, each said clone being identically profiled initially by a duplicate EMR of the virtual patient for separate diagnostic treatment by one of a plurality of simulation participants;
    at least one evaluator station operably coupled to said simulation management unit, said evaluator station establishing interactive interface thereto for an evaluator;
    a plurality of participant stations operably coupled to said simulation management unit, each said participant station establishing interactive access for one of said simulation participants to a corresponding one of said duplicate EMRs during a simulated clinical encounter with a corresponding clone of the virtual patient;
    wherein said simulation management unit independently updates said EMRs of the clones for said simulation participants responsive to clinical actions respectively taken thereby based on said simulated clinical encounters with said clones of the virtual patient.

2. The interactive evaluation system as recited in claim 1, wherein said EMR items include at least one modifiable medical form and auxiliary documentation, said auxiliary documentation having at least one item selected from the group consisting of: X-ray images, CAT scan results, MRI results, labs, orders, and SOAP notes.

3. The interactive evaluation system as recited in claim 1, wherein a plurality of said templates stored in said database are selectively customizable to form EMR items each respectively formatted according to a predetermined Medical Institute form.

4. The interactive evaluation system as recited in claim 1, wherein said database stores each of said EMR items as an undivided data element in a designated field of said database.

5. The interactive evaluation system as recited in claim 1, wherein said simulation management unit maintains at least one of said updated duplicated EMRs in said database to define a base condition of said virtual patient for a subsequent simulation scenario.

6. The interactive evaluation system as recited in claim 1, wherein said simulation management unit includes an evaluation module executable to apply a plurality of predetermined evaluative criteria to clinical actions taken by each simulation participant to provide a grading assessment therefor.

7. The interactive evaluation system as recited in claim 1, wherein said simulation management unit includes a third control module executable to harvest updates to at least one said duplicate EMR reflecting clinical actions undertake by at least one simulation participant, said third control module characterizing said harvested updates according to a predetermined statistical analysis.

8. The interactive evaluation system as recited in claim 1, wherein at least one of said participant stations includes a video camera device for video capture of at least one said simulated clinical encounter.

9. The interactive evaluation system as recited in claim 1 wherein at least one of said control modules of said simulation management unit executes responsive to said evaluator station to selectively configure each said duplicate EMR for restricting access thereto by said participant.

10. The interactive evaluation system as recited in claim 1, wherein at least one of said control modules of said simulation management unit executes responsive to said evaluator station to establish a roster of live actors, said control module being executable to selectively assign one of the live actors to emulate the virtual patient for at least one said simulated clinical encounter.

11. The interactive evaluation system as recited in claim 1, wherein said simulation management unit is executable to define said EMR of the virtual patient responsive to specification of said simulation scenario by said evaluator, said EMR being thereby populated with EMR items medically correlated to said specified simulation scenario, said EMR items being collectively indicative of a target diagnosis.

12. The interactive evaluation system as recited in claim 1, wherein said simulation management unit executes responsive to said participant station to independently maintain each said duplicate EMR, each said duplicate EMR being independently updated responsive to clinical actions taken by a corresponding one of said simulation participants.

13. An interactive educational system for simulating clinical care of a virtual patient comprising:
 a database of electronic medical records, at least one said electronic medical record (EMR) including a plurality of EMR items collectively profiling the virtual patient in a base condition;
 a simulation management unit coupled to said database, said simulation management unit including a plurality of selectively executable control modules;
  at least a first of said control modules being executable to define a simulation scenario with respect to the virtual patient;
  at least a second of said control modules being executable to generate for a plurality of students a respective plurality of duplicate EMRs each corresponding to a clone of the virtual patient in the base condition, each said clone being identically profiled initially by a duplicate EMR for separate diagnostic treatment by one of the students;
 at least one faculty station operably coupled to said simulation management unit, said faculty station establishing interactive interface thereto for an instructor;
 a plurality of student stations operably coupled to said simulation management unit, each said student station establishing interactive access for one of said students to a corresponding one of said duplicate EMRs during a simulated clinical encounter with one said virtual patient clone;
 wherein said simulation management unit independently updates said duplicate EMR for each said virtual patient clone according to a clinical action responsively taken by a corresponding student based on said simulated clinical encounter therewith; an independently updated EMR being thereby generated for each of said virtual patient clones.

14. The interactive educational system as recited in claim 13, wherein said simulation management unit maintains at least one of said updated EMRs of said virtual patient clones in said database to define the base condition of the virtual patient for a subsequent simulation scenario.

15. The interactive educational system as recited in claim 14, wherein said simulation management unit includes an evaluation module executable to apply a plurality of predetermined evaluative criteria to clinical actions taken by each student to provide a grading assessment therefor.

16. The interactive educational system as recited in claim 15, wherein said simulation management unit includes at least one control module executable to harvest updates to at least one said duplicate EMR reflecting clinical actions undertake by at least one student, said control module characterizing said harvested updates according to a predetermined statistical analysis.

17. The interactive educational system as recited in claim 16, wherein at least one of said control modules of said simulation management unit executes responsive to said faculty station to establish a roster of live actors, said control module being executable to selectively assign one of the live actors to emulate the virtual patient for at least one said simulated clinical encounter.

18. An interactive system for progressively simulating clinical care of a persistent virtual patient comprising:
 a database of electronic medical records, at least one said electronic medical record (EMR) including a plurality of EMR items collectively profiling the virtual patient in a base condition;
 a simulation management unit coupled to said database, said simulation management unit including a plurality of selectively executable control modules;
  at least a first of said control modules being executable to define a simulation scenario with respect to the virtual patient;
  at least a second of said control modules being executable to generate respectively for a plurality of simulation participants a plurality of duplicate EMRs corresponding to clones of the virtual patient in the base condition, each said clone being identically profiled initially by a duplicate EMR for separate diagnostic treatment by one of the simulation participants;
 at least one evaluator station operably coupled to said simulation management unit, said evaluator station establishing interactive interface thereto for an evaluator;
 a plurality of simulation participant stations operably coupled to said simulation management unit, each said simulation participant station establishing interactive access for one of said simulation participants to a corresponding one of said duplicate EMRs during a simulated clinical encounter with one said virtual patient clones;
 wherein said simulation management unit independently updates said duplicate EMR for each said virtual patient clone according to a clinical action responsively taken by a corresponding simulation participant based on said simulated clinical encounter therewith, an independently updated EMR being thereby generated for each of said virtual patient clones;

wherein said simulation management unit maintains said updated EMR of at least one selected virtual patient clone in said database to define the base condition of the virtual patient for a subsequent simulation scenario, said second control module thereby generating said plurality of duplicate EMRs to correspond in said subsequent simulation scenario to further clones of said selected virtual patient.

19. The interactive system as recited in claim 18, wherein said simulated clinical encounter includes a live standard patient emulating said virtual patient clone therein.

20. The interactive system as recited in claim 18, wherein said simulated clinical encounter includes a manikin configured to emulate said virtual patient clone therein.

21. A method of interactively simulating and evaluating clinical care of a virtual patient comprising:
  establishing a database of electronic medical records, at least one said electronic medical record (EMR) including a plurality of EMR items collectively profiling the virtual patient;
  actuating a simulation management unit established in a processor operably coupled to said database, said simulation management unit actuation including selective execution of a plurality of control modules programmed therein;
    at least a first of said control modules being selectively executed to define a simulation scenario with respect to the virtual patient;
    at least a second of said control modules being selectively executed to generate a plurality of clones of the virtual patient, each said clone being identically profiled initially by a duplicate EMR of the virtual patient for separate diagnostic treatment by one of a plurality of simulation participants;
  maintaining at least one interactive evaluator station interface to said simulation management unit;
  establishing for each said simulation participant an interactive participant station interface to said simulation management unit, each said simulation participant thereby having interactive access to a corresponding one of said duplicate EMRs during a simulated clinical encounter with a corresponding clone of the virtual patient;
  said simulation management unit independently updating said EMRs of the clones for said simulation participants responsive to clinical actions respectively taken thereby based on said simulated clinical encounters with said clones of the virtual patient.

22. The method as recited in claim 21 further comprising customizing a plurality of generic templates stored in said database according to a predetermined EMR format of a preselected institution, said EMR items being established thereby with visual indicia identifying said preselected institution.

23. The method as recited in claim 21, wherein an update to each said duplicate EMR is stored by said simulation management unit in time stamped manner for a corresponding one of said simulation participants, a targeted evaluation of said simulation participant being thereby enabled.

24. The method as recited in claim 21 further comprising executing said simulation management unit responsive to said interactive evaluator station to provide remedial feedback with respect to an update made to at least one said duplicate EMR based on said simulated clinical encounter.

25. The method as recited in claim 21 further comprising executing said simulation management unit responsive to said interactive evaluator station to define a series of ideal states for said EMR to progress through during said simulation scenario; and, respectively evaluating said duplicate EMRs of said simulation participants according to said ideal states.

26. The method as recited in claim 21 further comprising a live actor emulating at least one said virtual patient clone; and, executing said simulation management unit to capture feedback from the live actor based on said simulated clinical encounter.

27. The method as recited in claim 21 further comprising executing said simulation management unit to update at least one of said duplicate EMRs to emulate natural progression of said virtual patient clone in medical condition between time-displaced ones of said simulated clinical encounters of said simulation scenario.

28. The method as recited in claim 27, wherein said virtual patient clone is projected in medical condition by said simulation management unit according to therapeutic actions taken by a corresponding simulation participant to reflect probable results of the therapeutic action.

29. A method for progressively simulating clinical care of a persistent virtual patient comprising:
  establishing a database of electronic medical records, at least one said electronic medical record (EMR) including a plurality of EMR items collectively profiling the virtual patient in a base condition;
  actuating a simulation management unit established in a processor operably coupled to said database, said simulation management unit actuation including selective execution of a plurality of control modules programmed therein;
    at least a first of said control modules being executable to define a simulation scenario with respect to the virtual patient;
    at least a second of said control modules being executable to respectively generate for a plurality of simulation participants a plurality of duplicate EMRs corresponding to clones of the virtual patient in the base condition, each said clone being identically profiled initially by a duplicate EMR for separate diagnostic treatment by one of the simulation participants;
  maintaining at least one evaluator station interface to said simulation management unit;
  establishing for each said simulation participant an interactive participant station interface to said simulation management unit, each said simulation participant thereby having interactive access to a corresponding one of said duplicate EMRs during a simulated clinical encounter with one said virtual patient clones;
  independently updating said duplicate EMR for each said virtual patient clone according to a clinical action responsively taken by a corresponding simulation participant based on said simulated clinical encounter therewith, an independently updated EMR being thereby generated for each of said virtual patient clones; and,
  selectively maintaining in said database said updated EMR of at least one of said virtual patient clones selected for persistent simulation, said updated EMR of said selected virtual patient clone defining the virtual patient base condition for a subsequent simulation scenario, said second control module thereby generating said plurality of duplicate EMRs to correspond in said subsequent simulation scenario to further clones of said selected virtual patient.

* * * * *